United States Patent
Fagète et al.

(10) Patent No.: US 10,689,461 B2
(45) Date of Patent: Jun. 23, 2020

(54) ANTIBODY DUAL DISPLAY DUAL COMPOSITIONS AND METHODS OF USE THEREOF

(71) Applicant: NovImmune SA, Geneva (CH)

(72) Inventors: Séverine Fagète, Cernex (FR); Oliver Hartley, Carouge (CH); Nicolas Fischer, Geneva (CH)

(73) Assignee: NovImmune SA, Geneva (CH)

( * ) Notice: Subject to any disclaimer, the term of this patent is extended or adjusted under 35 U.S.C. 154(b) by 139 days.

(21) Appl. No.: 15/706,291

(22) Filed: Sep. 15, 2017

(65) Prior Publication Data

US 2018/0134809 A1    May 17, 2018

Related U.S. Application Data

(60) Provisional application No. 62/395,139, filed on Sep. 15, 2016.

(51) Int. Cl.
| | |
|---|---|
| C40B 40/02 | (2006.01) |
| C07K 16/46 | (2006.01) |
| C07K 16/00 | (2006.01) |
| G01N 33/53 | (2006.01) |
| C07K 16/08 | (2006.01) |

(52) U.S. Cl.
CPC .......... *C07K 16/468* (2013.01); *C07K 16/005* (2013.01); *C07K 16/08* (2013.01); *G01N 33/53* (2013.01); *C07K 2317/10* (2013.01); *C07K 2317/24* (2013.01); *C07K 2317/31* (2013.01); *C07K 2317/32* (2013.01); *C07K 2317/35* (2013.01); *C07K 2317/622* (2013.01); *C07K 2317/626* (2013.01); *C07K 2319/70* (2013.01); *C40B 40/02* (2013.01)

(58) Field of Classification Search
None
See application file for complete search history.

(56) References Cited

FOREIGN PATENT DOCUMENTS

| | | |
|---|---|---|
| EP | 0 404 097 B1 | 9/1996 |
| WO | WO 93/11161 A1 | 6/1993 |
| WO | WO 2011/121110 A1 | 10/2011 |

OTHER PUBLICATIONS

De Kruif, J. and T. Logtenberg (Mar. 29, 1996) "Leucine Zipper Dimerized Bivalent and Bispecific scFv Antibodies from a Semisynthetic Antibody Phage Display Library" *J Biol Chem*, 271(13):7630-7634.
Fagète, S. et al. (2009) "Specificity tuning of antibody fragments to neutralize two human chemokines with a single agent" *mAbs*, 1(3):288-296.
Fagète, S. et al. (2017) "Dual display: phage selection driven by co-engagement of two targets by two different antibody fragments" *Prot Eng Des Sel*, 30(9):575-582.
Holliger et al. (Jul. 1993) "'Diabodies': Small bivalent and bispecific antibody fragments" *Proc Natl Acad Sci USA*, 90:6444-6448.

(Continued)

*Primary Examiner* — Christian C Boesen
(74) *Attorney, Agent, or Firm* — Cooley LLP; Ivor R. Elrifi; Cynthia A. Kozakiewicz

(57) ABSTRACT

Provided herein are display systems for simultaneously displaying two different ligand binding polypeptides at the surface of a phage. Also provided are kits, methods of using such display systems and methods of discovering novel bispecific antibodies.

17 Claims, 15 Drawing Sheets

Specification includes a Sequence Listing.

(56) References Cited

OTHER PUBLICATIONS

Hoogenboom, H.R. et al. (1991) "Multi-subunit proteins on the surface of filamentous phage: methodologies for displaying antibody (Fab) heavy and light chains" *Nucleic Acids Res*, 19(15):4133-4137.
Lee, C.V. et al. (2004) "Bivalent antibody phage display mimics natural immunoglobulin" *J Immunol Meth*, 284:119-132.
Magistrelli, G. et al. (2010) "Rapid, simple and high yield production of recombinant proteins in mammalian cells using a versatile episomal system" *Protein Expr Purif*, 72:209-216.
McGuinness, B.T. et al. (1996) "Phage diabody repertoires for selection of large numbers of bispecific antibody fragments" *Nat Biotechnol*, 14:1149-1154.
Moll, J.R. et al. (2001) "Designed heterodimerizing leucine zippers with a range of pIs and stabilities up to $10^{-15}$ M" *Protein Sci*, 10:646-655.
Genbank Accession No. NM_000579.3, "*Homo sapiens* C-C motif chemokine receptor 5 (gene/pseudogene) (CCR5), transcript variant A, mRNA" Modification Date: Dec. 23, 2018. National Center for Biotechnology Information (NCBI) [online]. Retrieved from the Internet: https://www.ncbi.nlm.nih.gov/nuccore/NM_000579.3; retrieved on Jan. 15, 2019, 6 pages.
Genbank Accession No. NM_000733.3, "*Homo sapiens* CD3e molecule (CD3E), mRNA" Modification Date: Oct. 20, 2018. National Center for Biotechnology Information (NCBI) [online]. Retrieved from the Internet: https://www.ncbi.nlm.nih.gov/nuccore/NM_000733.3; retrieved on Jan. 15, 2019, 4 pages.
Genbank Accession No. NM_173953.2, "Bos taurus prolactin (PRL), mRNA" Modification Date: Oct. 20, 2018. National Center for Biotechnology Information (NCBI) [online]. Retrived from the Internet: https://www.ncbi.nlm.nih.gov/nuccore/NM_173953.2; retrieved on Jan. 15, 2019, 3 pages.
Pande, J. et al. (2010) "Phage display: Concept, innovations, applications and future" *Biotechnol Adv*, 28:849-858.
Ravn, U. et al. (2010) "By-passing in vitro screening—next generation sequencing technologies applied to antibody display and in silico candidate selection" *Nucl Acids Res*, 38(21):e193, 11 pages.
Trkola, A. et al. (Jan. 2001) "Potent, Broad-Spectrum Inhibition of Human Immunodeficiency Virus Type 1 by the CCR5 Monoclonal Antibody Pro 140" *J Virol*, 75(2):579-588.
Venet, S. et al. (2012) "Transferring the Characteristics of Naturally Occurring and Biased Antibody Repertoires to Human Antibody Libraries by Trapping CDRH3 Sequences" *PLoS One*, 7(8):e43471, 12 pages.
Vieira, J. and J. Messing (1987) "Production of Single-Stranded Plasmid DNA" *Methods Enzymol*, 153:3-11.
Wang, X. et al. (Apr. 28, 2011) "Antibody Engineering Using Phage Display with a Coiled-Coil Heterodimeric Fv Antibody Fragment" *PLoS One*, 6(4):e19023, 8 pages.
Waterhouse, P. et al. (1993) "Combinatorial infection and in vivo recombination: a strategy for making large phage antibody repertoires" *Nucl Acids Res*, 21(9):2265-2266.
Zapata, G. et al. (1995) "Engineering linear F(ab')$_2$ fragments for efficient production in *Escherichia coli* and enhanced antiproliferative activity" *Protein Eng*, 8(10):1057-1062.

Figure 10A

```
5'  GGAATTGTGAGCGGATAACAATTCCCCTGTAGAAATAATTTTGTTTAACTTTAATAAGGAGATAT
    |+++++++++++++|+++++++++++++|+++++++++++++|+++++++++++++|+++++++++++++|++++++  65
3'  CCTTAACACTCGCCTATTGTTAAGGGGACATCTTTATTAAAACAAATTGAAATTATTCCTCTATA
    [lac operator]                              ↑                    [RBS]
                                         SphI site insertion NcoI
    ACCATGGCACATCACCACCACCATCACGTGGGTACCGGTTCGAATGATGACGACGACAAGAGTCC
    |+++++++++++++|+++++++++++++|+++++++++++++|+++++++++++++|+++++++++++++|++++++  130
    TGGTACCGTGTAGTGGTGGTGGTAGTGCACCCATGGCCAAGCTTACTACTGCTGCTGTTCTCAGG
                                         [MCS]

BamHI                                         SalI   HindIII  NotI
    GGATCCCAATTGGGAGCTCGTGTACACGGCGCGCCTGCAGGTCGACAAGCTTGCGGCCGCACTCG
    |+++++++++++++|+++++++++++++|+++++++++++++|+++++++++++++|+++++++++++++|++++++  195
    CCTAGGGTTAACCCTCGAGCACATGTGCCGCGCGGACGTCCAGCTGTTCGAACGCCGGCGTGAGC
                                         [MCS]

AGTCTGGTAAAGAAACCGCTGCTGCGAAATTTGAACGCCAGCACATGGACTCGTCTACTAGCGCA
    |+++++++++++++|+++++++++++++|+++++++++++++|+++++++++++++|+++++++++++++|++++++  260
    TCAGACCATTTCTTTGGCGACGACGCTTTAAACTTGCGGTCGTGTACCTGAGCAGATGATCGCGT
                                         [MCS]

PacI AvrII
    GCTTAATTAACCTAGGCTGCTGCCACCGCTGAGCAATAACTAGCATAACCCCTTGGGGCCTCTAA
    |+++++++++++++|+++++++++++++|+++++++++++++|+++++++++++++|+++++++++++++|++++++  325
    CGAATTAATTGGATCCGACGACGGTGGCGACTCGTTATTGATCGTATTGGGGAACCCCGGAGATT
    [MCS]                                      [T7 terminator]

ACGGGTCTTGAGGGGTTTTTTG    3'  SEQ ID NO: 15
    |+++++++++++++|+++++++|        347
    TGCCCAGAACTCCCCAAAAAAC    5'  SEQ ID NO: 16
    [T7 terminator]
```

ANTIBODY DUAL DISPLAY DUAL COMPOSITIONS AND METHODS OF USE THEREOF

RELATED APPLICATIONS

The application claims the benefit of U.S. Provisional Application No. 62/395,139 filed Sep. 15, 2016. The content of this application is hereby incorporated by reference in its entirety.

INCORPORATION-BY-REFERENCE OF SEQUENCE LISTING

The contents of the text file submitted electronically herewith are incorporated herein by reference in their entirety: A computer readable format copy of the Sequence Listing (filename: NOVI-042 001US 322145-2654 SUBSTITUTE SEQ LIST_ST25_R, date recorded: Sep. 17, 2019; 10 kilobytes).

FIELD OF THE INVENTION

The present invention relates to generally to the field of antibody phage display compositions and methods that enable pairs of antibodies to be co-selected based on co-engagement of their respective targets. The compositions and methods embodied in the present invention are useful for the development of bispecific antibodies.

BACKGROUND OF THE INVENTION

Phage display is a powerful in vitro evolution technology that enables rare ligands with desired characteristics to be isolated from large libraries of variants encoded by and expressed at the surface of filamentous bacteriophage. Many antibodies identified via phage display are currently used therapeutically or are in clinical development. While antibody phage display has been used to discover bispecific antibodies to date, the process has not streamlined to insure that selection is based on co-engagement. Moreover, other techniques known in the art (e.g., phage diabody technology) have not been used for direct selection based on co-engagement and broader application of phage diabody technology may not be possible due to difficulties in constructing diabody repertoires. Differences in the antigen binding site geometry of diabodies versus immunoglobulin molecules may compromise their utility for translation into immunoglobulin-based bispecific antibody formats.

Thus, there exists a need for phage display compositions and methods that allow for pairs of antibodies to be co-selected based on co-engagement of their respective targets.

SUMMARY OF THE INVENTION

Provided herein are display systems for simultaneously displaying two ligand binding polypeptides at the surface of a phage. Such systems include a phagemid containing the coding sequence of a first ligand binding polypeptide fused in frame to a first dimerization domain and to an outer surface protein of the phage; a plasmid containing the coding sequence of a second ligand binding polypeptide fused in frame to a second dimerization domain; and a helper phage containing coding sequences of all proteins necessary for packaging the phage. In these systems, the first and second ligand binding polypeptides are different and each bind to a different target ligand. When the first and second ligand binding polypeptide fusions and all phage proteins are expressed in a suitable host cell, the two ligand binding polypeptide fusions associate via their respective dimerization domains, resulting in simultaneous display of the two ligand binding polypeptides at the surface of phage.

In one embodiment, the first ligand binding polypeptide and dimerization domain is fused to the minor coat protein 3 of filamentous bacteriophage, which heterodimerizes to the second dimerization domain with high affinity. Both the first and second dimerization domains are leucine zippers.

In some embodiments, the first dimerization domain is encoded by the nucleic acid sequence of SEQ ID NO: 1 and the second dimerization domain is encoded is encoded by the nucleic acid of SEQ ID NO: 3 or the first dimerization domain contains the amino acid sequence of SEQ ID NO: 2 and the second dimerization domain comprises the amino acid sequence SEQ ID NO: 4. In other embodiments, the first dimerization domain is encoded by the nucleic acid sequence of SEQ ID NO: 5 and the second dimerization domain is encoded by the nucleic acid of SEQ ID NO: 7 or the first dimerization domain contains the amino acid sequence of SEQ ID NO: 6 and the second dimerization domain comprises the amino acid sequence SEQ ID NO: 8

In these systems, the first and second ligand binding polypeptides can be antigen binding polypeptides for example, scFvs and non-immunoglobulin binding domains.

When the first and second ligand binding polypeptides are expressed in a host cell, the two ligand binding polypeptides displayed on the surface of the phage have a geometry comparable to that of an IgG molecule, have a molecular separation distance comparable to that of an IgG molecule, or have both a geometry and molecular separation distance comparable to that of an IgG molecule.

Also provided herein are kits of the display system in a suitable packaging along with instructions for use.

Also provided are methods for displaying two ligand polypeptides on the surface of a phage by causing any of the display system described herein to be transcribed and translated into a suitable host cell.

Additionally, methods are provided for detecting a simultaneous specific interaction between one or more test agents and the two ligand binding polypeptides displayed on the surface of a phage. In such methods, phages displaying the two or more ligand binding polypeptides displayed on the surface using the display systems described herein are contacted with the one or more test agents under conditions suitable to produce a stable complex between the ligand binding polypeptides and the one or more test agents and the formation of a stable complex (if any) is detected. In various embodiments, the one or more test agents are protein, polysaccharide, and/or ligand. For example, the one or more test agents may be antigens or ligands.

BRIEF DESCRIPTION OF THE DRAWINGS

In FIG. 1A, sequences of the complementary leucine zipper domains (Z1, SEQ ID NO: 2 and Z2, SEQ ID NO: 4) are provided. FIG. 1B is schematic representation of the two-replicon expression system used to produce dual-display phage.

FIG. 3A shows a schematic of the phage clones encoding either anti-IFNγ-Z1 or anti-IFNγ-Z2 as the phage component were subjected to rounds of selection consisting of infection and rescue in *E. coli* expressing anti-CD3-Z2 as the soluble component followed by panning against immobilized CD3 peptide. Only phage with the anti-IFNγ-Z2 phage component would be expected to have the capacity to acquire the anti-CD3-Z1 soluble component. FIG. 3B shows the results of ELISA assay for binding to immobilized CD3 peptide is performed on the initial phage mixture as well as on phage populations obtained after each round of selection. Three different selection experiments are performed with the IFNγ-Z2 phage initially diluted in IFNγ-Z1 phage at 1:10, 1:1000 and 1:100000. FIG. 3C shows the results of ELISA assay as in FIG. 3B except that selection rounds were carried out without panning on immobilized CD3 peptide.

In FIG. 4A, four phage clones capable of engaging CCR5 alone, CD3 peptide alone, both structures or neither structure were used, together with cells expressing CCR5 tagged with the CD3 peptide. FIG. 4B is a flow chart depicting the selection process.

FIG. 10A shows the sequence modifications made to pCDF-1b to generate pCDF-1b-DD, the sequence from pCDF-1b showing the multiple cloning site (MCS) plus flanking regions (SEQ ID NOs: 15 and 16). The site of insertion of the SphI site is indicated with an arrow.

DETAILED DESCRIPTION

Figure 1:
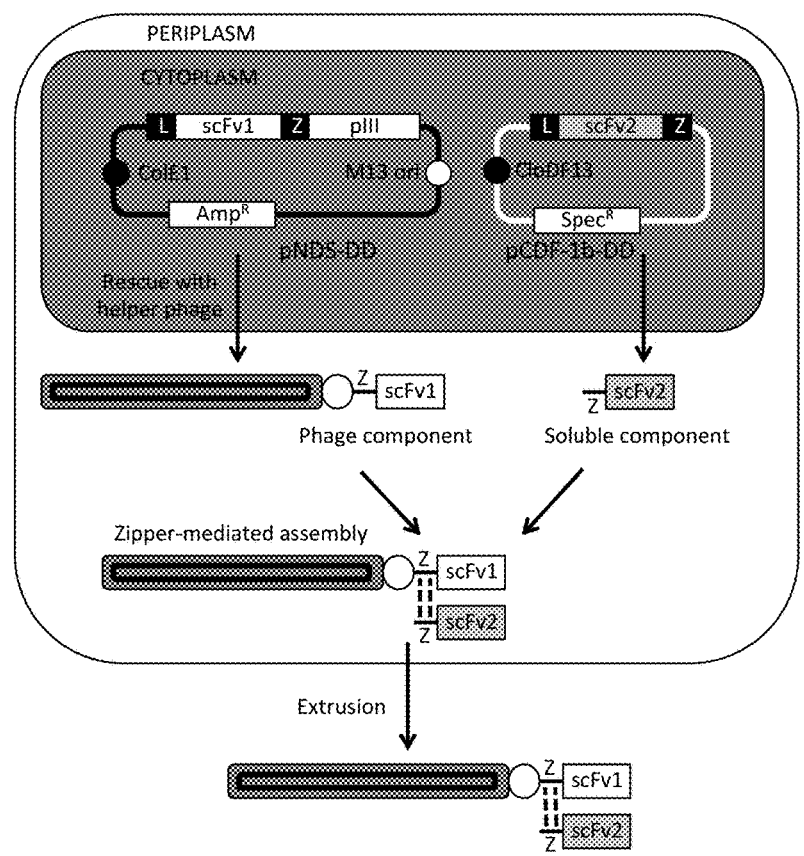
FIGS. 1A-B provide an overview of the dual-display system.

Provided herein are phage display systems, compositions, and methods for the dual-display of two different ligand binding polypeptides (i.e., antibodies or antigen binding fragments thereof), on the surface of the phage (e.g., a filamentous bacteriophage). When the system is expressed in a suitable host cell, the two polypeptides have a geometry and/or molecular separations distance that resembles that of the two antigen binding sites on an intact immunoglobulin. These systems, compositions, and methods use a dual replicon system that is readily compatible with the use of large naive antibody repertoires and can be used to co-engage two different user-defined targets.

Definitions

Unless otherwise defined, scientific and technical terms used in connection with the present invention shall have the meanings that are commonly understood by those of ordinary skill in the art, further unless otherwise required by context, singular terms shall include pluralities and plural terms shall include singular. Generally, nomenclature utilized in connection with and techniques of cell and tissue culture, molecular biology and protein and oligo- or polypeptide chemistry and hybridization described herein and those well-known and commonly used in the art. Standard techniques are used for recombinant DNA, oligonucleotide synthesis, and tissue culture and transformation (e.g., electroporation, lipofectin). Enzymatic reactions and purification techniques are performed according to manufactures specifications or as commonly accomplished in the art as described herein. The foregoing techniques and procedures are generally performed according to the conventional methods well known in the art and as described herein in various general and more specific references that are cited and discussed throughout the present specification. (See, e.g., Sambrook et al., Molecular Cloning. A Laboratory Manual).

In the context of the present application, the following terms are defined in the following manner:

The term "antibody", as used herein, refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) contains four polypeptide chains, two heavy (H) chains and two light (L) chains inter-connected by disulfide bonds. The immunoglobulins represent a large family of molecules that include several types of molecules, such as IgD, IgG, IgA, IgM and IgE.

As used herein, the term "bispecific antibody" refers to an artificial protein that is composed of fragments of two different monoclonal antibodies and consequently binds to two different types of antigen.

The term "immunoglobulin molecule" includes, for example, hybrid antibodies, or altered antibodies, and fragments thereof.

"Antigen" as used herein refers to a substance that is recognized and bound specifically by an antibody. Antigens can include, for example, peptides, proteins, glycoproteins, polysaccharides and lipids; equivalents and combinations thereof. As used herein, the term "surface antigens" refers to the plasma membrane components of a cell and encompasses the integral and peripheral membrane proteins, glycoproteins, polysaccharides and lipids that constitute the plasma membrane. An "integral membrane protein" is a transmembrane protein that extends across the lipid bilayer of the plasma membrane of a cell. A typical integral membrane protein contains at least one "membrane spanning segment" that generally comprises hydrophobic amino acid residues. Peripheral membrane proteins do not extend into the hydrophobic interior of the lipid bilayer and are bound to the membrane surface by noncovalent interaction with other membrane proteins.

"Antibody fragments" include a portion of an intact antibody, preferably with the antigen binding or variable region of the intact antibody. Examples of antibody fragments include, but are not limited to, Fab, Fab', F(ab')2, and Fv fragments; diabodies; linear antibodies (See Zapata et al., Protein Eng. 8(10): 1057-1062 (1995)); single-chain antibody molecules; and multispecific antibodies formed from antibody fragments.

A single-chain variable fragment (scFv) is typically a fusion protein of the variable regions of the heavy (VH) and light chains (VL) of immunoglobulins that are connected with a short linker peptide of 10 to about 25 amino acids. The linker is usually rich in glycine for flexibility, as well as serine or threonine for solubility. The linker can either connect the N-terminus of the VH with the C-terminus of the VL, or vice versa.

"Diabodies" refer to small antibody fragments with two antigen-binding sites, which include a heavy-chain variable domain (VH) connected to a light-chain variable domain (VL) in the same polypeptide chain (VW-VL). By using a linker that is too short to allow pairing between the two domains on the same chain, the domains are forced to pair with the complementary domains of another chain and create two antigen-binding sites. Diabodies are described more fully in, for example, EP 404,097; WO 93111161; and Hollinger et al., Proc. Natl. Acad. Sci. USA, 90:6444-6448 (1993), which are incorporated herein by reference "Domain" refers to a portion of a protein that is physically or functionally distinguished from other portions of the protein or peptide. Physically-defined domains include those amino acid sequences that are exceptionally hydrophobic or hydrophilic, such as sequences that are membrane-associated or cytoplasm-associated. Domains may also be defined by internal homologies that arise, for example, from gene duplication. Functionally-defined domains have a distinct biological function(s). For instance, the ligand-binding domain of a receptor is the domain that binds a ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain. A "membrane anchorage domain" refers to the portion of a protein that mediates membrane association. Generally, the membrane anchorage domain is composed of hydrophobic amino acid residues. Alternatively, the membrane anchorage domain may contain modified amino acids, e.g. amino acids that are attached to a fatty acid chain, which in turn anchors the protein to a membrane.

A "ligand" is a molecule capable of being bound by a particular domain (i.e., a "ligand-binding domain"). Suitable ligands may be chemically synthesized using any method used in the art or may occur in nature. A "ligand binding domain" is a domain whose action is dependent on the presence of bound ligand. In some cases, "ligand binding" to a receptor protein alters the chemical conformation by affecting the three-dimensional shape orientation. The rate of binding of a ligand to the ligand binding domain is known as its affinity.

As used herein "high affinity" refers to ligand binding resulting from greater intermolecular force between the ligand and its receptor. Thus, high-affinity binding involves a longer residence time for the ligand at its receptor binding site, and high-affinity ligand binding implies that a relatively low concentration of a ligand is adequate to maximally occupy a ligand-binding site and trigger a physiological response "Heterodimeric receptors" are cellular proteins, containing two proteinaceous subunits each of which exhibit binding affinity to a ligand. The two proteinaceous subunits are distinct molecules which differ in amino acid sequence by at least one amino acid residue.

As used herein, a "dimer" is a macromolecular complex formed by two non-covalently bound macromolecules, such as proteins, polypeptides, or nucleic acids. A "homodimer" is formed by two identical molecules in a process called "homodimerization". A "heterodimer" is formed by two different macromolecules in a process called "heterodimerization". A "dimerization domain" refers to the part of the molecule that mediates macromolecule association.

The terms "polypeptide", "peptide" and "protein" and the like are used interchangeably herein to refer to polymers of amino acids of any length. The polymer may be linear, cyclic, or branched, it may contain modified amino acids, and/or it may be interrupted by non-amino acids. These terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component.

As used herein, the term "amino acid" refers to either natural and/or unnatural or synthetic amino acids, including glycine and both the D or L optical isomers, and amino acid analogs and peptidomimetics.

"Peptide", as used herein, refers to a short polypeptide, e.g., one that typically contains less than about 50 amino acids and more typically less than about 30 amino acids. The term also encompasses analogs and mimetics that mimic structural and, thus, biological function.

The term "fusion protein" refers to a polypeptide containing a polypeptide or fragment coupled to heterologous amino acid sequences.

The terms "polynucleotide", "nucleic acid molecule", "nucleic acid", or "nucleic acid sequence" and the like refer to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. Nucleic acid can be in any topological conformation. For instance, the nucleic acid can be single-stranded, double-stranded, triple-stranded, quadruplexed, partially double-stranded, branched, hairpinned, circular, or in a padlocked conformation.

A "coding sequence" or "open reading frame" is a sequence of nucleotides that encodes a polypeptide or protein. The termini of the coding sequence are a start codon and a stop codon.

A "host cell" or "cell line" or "cell culture" or "cell" denotes bacterial, plant, insect or higher eukaryotic cells grown or maintained in vitro. The descendants of a cell may not be completely identical (either morphologically, genotypically, or phenotypically) to the parent cell.

The term "gene" means the segment of DNA involved in producing a protein. It includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a DNA nucleic acid sequence (e.g., a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell. (See Sambrook et al., Molecular Cloning: A Laboratory Manual, 18.1-18.88 (1989)). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the disclosure or individual domains of the polypeptides of the disclosure), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length or more preferably over a region that is 100 to 500 or 1000 or more nucleotides in length.

As used herein, "bacteriophage" refers to a virus that infects bacteria. Similarly, "archaeophage" refers to a virus that infects archaea. The term "phage" is used herein to refer to both types of viruses but, in certain instances, as indicated by the context may also be used as shorthand to refer to a bacteriophage or archaeophage specifically. Bacteriophage and archaeophage are obligate intracellular parasites (with respect to both the step of identifying a host cell to infect and to only being able to productively replicate their genome in an appropriate host cell) that infect and multiply inside bacteria/archaea by making use of some or all of the host biosynthetic machinery. Though different bacteriophages and archaeophages may contain different materials, they all contain nucleic acids and proteins, and can, under certain circumstances, be encapsulated in a lipid membrane.

Depending upon the phage, the nucleic acid may be either DNA or RNA (but typically not both) and it can exist in various forms, with the size of the nucleic acid depending on the phage. The simplest phage only have genomes a few thousand nucleotides in size, while the more complex phages may have more than 100,000 nucleotides in their genome, and, in rare instances, more than 1,000,000. Additionally, phages may be covered by a lipid membrane and may also contain different materials. The number of different kinds of protein and the amount of each kind of protein in the phage particle will vary depending upon the phage. The proteins protect the nucleic acid from nucleases in the environment and are functional in infection.

Many filamentous and non-filamentous phage genomes have been sequenced, including, for example, the filamentous phages M13, f1, fd, Ifl, Ike, Xf, Pf1, and Pf3. Within the class of filamentous phages, M13 is the most well-characterized species, as its 3-dimensional structure is known and the functions of its coat proteins are well-understood. Specifically, the M13 genome encodes five coat proteins pIII, VIII, VI, VII, and IX, which are used as sites for the insertion of foreign DNA into the M13 vectors.

As used herein, a "phage genome" includes naturally occurring phage genomes and derivatives thereof. Generally (though not necessarily), derivatives possess the ability to propagate in the same hosts as the parent. In some embodiments, the only difference between a naturally occurring phage genome and a derivative phage genome is the addition or deletion of at least one nucleotide from at least one end of the phage genome (if the genome is linear) or along at least one point in the genome (if the genome is circular).

As used herein, a "phage host cell" or "host cell" or the like is a cell that can form phage from a particular type of phage genomic DNA. In some embodiments, the phage genomic DNA is introduced into the cell by infection of the cell by a phage. The phage binds to a receptor molecule on the outside of the host cell and injects its genomic DNA into the host cell. In some embodiments, the phage genomic DNA is introduced into the cell using transformation or any other suitable techniques. In some embodiments, the phage genomic DNA is substantially pure when introduced into the cell. The phage genomic DNA can be present in a vector when introduced into the cell. By way of non-limiting example, the phage genomic DNA is present in a yeast artificial chromosome (YAC) that is introduced into the phage host cell by transformation or an equivalent technique. The phage genomic DNA is then copied and packaged into a phage particle following lysis of the phage host cell.

As used herein, "outer-surface sequences" refer to nucleotide sequences that encode "outer-surface proteins" of a genetic package. These proteins form a proteinaceous coat that encapsulates the genome of the genetic package. Typically, the outer-surface proteins direct the package to assemble the polypeptide to be displayed onto the outer surface of the genetic package, e.g. a phage or bacteria.

The "gene-3 minor coat protein (P3)" (a phage outer surface protein) is required for release from the filamentous bacteriophage assemble at the host membrane and subsequently, for recognition and infection of a new host. P3 contains at least three distinct domains: two N-terminal domains that mediate host recognition and infection, and a C-terminal domain (P3-C) that is required for release from the host cell following phage assembly and contributes to the structural stability of the phage particle.

As used herein the term "phagemid" refers to a plasmid that contains an f1 origin of replication (ori) from an f1 phage. (See Analysis of Genes and Genomes, John Wiley & Sons, S. 140 (2004)). Phagemids can be used as a type of cloning vector in combination with filamentous phage M13, can be replicated as a plasmid, and also can be packaged as single stranded DNA in viral particles. Phagemids may contain an ori for double stranded replication, as well as an f1 ori to enable single stranded replication and packaging into phage particles A "phagemid system" requires fusion of an exogenous nucleic acid sequence to at least part of a phage outer-surface sequence (e.g., the coat sequence). In this way, upon infection in a suitable host cell, the exogenous sequence can be expressed on the surface of the phage. Typically, phage outer surface sequences most commonly used are within genes III and VIII of M13 bacteriophage, although genes VI, VII and IX fusions can also be used.

As used herein, "the helper phage" refers to a vector containing coding sequences for proteins necessary for packaging of the phage.

Dual Display Systems

Provided herein are display systems that allow robust display of two different ligand binding polypeptides (e.g., antibodies or antibody fragments) on the surface of a phage (i.e., a filamentous bacteriophage). When expressed in a suitable host cell, the two polypeptides have a geometry and/or a molecular separation distance that resembles that of the two antigen binding sites on an intact immunoglobulin molecule. These systems can be used in methods of identifying bispecific antibodies capable of specifically binding to target molecules of choice.

The display systems described herein include three separate components: (1) a phagemid encoding a first ligand binding polypeptide fused in frame to a first dimerization domain and an outer surface protein of the phage; (2) a plasmid encoding a second ligand binding polypeptide fused in frame to a second dimerization domain; and (3) a helper phage encoding all of the proteins necessary for packaging the phage. In these systems the first and second ligand binding polypeptides are different and each bind to a different target ligand.

These systems utilize cognate pairs of leucine zippers that preferentially heterodimerize with each other and only homodimerize with low affinity (if at all). Non-limiting examples of such leucine zippers include the engineered VBP domains of BZIP1 and BZIP2 (see Moll et al., Protein Science 10:646-655 (2001)) and the naturally occurring GABAB receptor 1 and 2 domains (see Wang et al., PLOS ONE 6(4): e19023 (2011). The sequences of these leucine zippers are provided below:

BZIP-1
(SEQ ID NO: 1)
CTGGAAATTCGCGCGGCGTTTCTGCGCCAGCGCAACACCGCGCTGCGCAC

CGAAGTGGCGGAACTGGAACAGGAAGTGCAGCGCCTGGAAAACGAAGTGA

GCCAGTATGAAACCCGCTATGGCCCGCTGGGCGGCGGCAAA (SEQ ID NO: 2)
LEIRAAFLRQRNTALRTEVAELEQEVQRLENEVSQYETRYGPLGGGK

BZIP-2
(SEQ ID NO: 3)
CTGGAAATTGAAGCGGCGTTTCTGGAACGCGAAAACACCGCGCTGGAAAC

CCGCGTGGCGGAACTGCGCCAGCGCGTGCAGCGCCTGCGCAACCGCGTGA

GCCAGTATCGCACCCGCTATGGCCCGCTGGGCGGCGGCAAA (SEQ ID NO: 4)
LEIEAAFLERENTALETRVAELRQRVQRLRNRVSQYRTRYGPLGGGK

GABA-R1
(SEQ ID NO: 5)
GAAGAAAAAGCCGCCTGCTGGAAAAAGAAACCGCGAACTGGAAAAAAT

TATTGCGGAAAAAGAAGAACGCGTGAGCGAACTGCGCCATCAGCTGCAGA

GC (SEQ ID NO: 6)
EEKSRLLEKENRELEKIIAEKEERVSELRHQLQS

GABA-R2
(SEQ ID NO: 7)
ACCAGCCGCCTGGAAGGCCTGCAGAGCGAAAACCATCGCCTGCGCATGAA

AATTACCGAACTGGATAAAGATCTGGAAGAAGTGACCATGCAGCTGCAGG

AT (SEQ ID NO: 8)
TSRLEGLQSENHRLRMKITELDKDLEEVTMQLQD

Upon expression in a suitable host cell, the two ligand binding polypeptide fusions associate via their respective dimerization domains, thereby resulting in simultaneous display of the two ligand binding polypeptides at the surface of the phage. Fusion of the first and second ligand binding domains in frame to one of the cognate pairs of leucine zippers insures that, upon expression in a suitable host cell, one copy of each of the ligand binding polypeptides is expressed on the surface of the phage.

These systems can also be used to display two different ligand binding polypeptides on the surface of a phage by causing the display system to be transcribed and translated in a suitable host cell (e.g., using any methods commonly employed in the art).

Also provided are methods for detecting a simultaneous specific interaction between one or more test agent and two ligand binding polypeptides displayed on the surface of a phage. In such methods, the phage is contacted with the test agent under conditions suitable to produce a stable complex between the ligand binding polypeptides and the one or more test agents. In various embodiments, the one or more test agents are antigen or a ligand (e.g., protein, a polysaccharide, and/or a lipid).

Accordingly, these display systems have potential to be applied to the identification of pairs of ligands capable of co-engaging two different user-defined targets, which would in turn facilitate the discovery of novel bispecific antibodies.

Building a Dual Replicon System Based on Leucine Zipper Heterodimerization Domains For display of two different scFvs in proximity at the phage surface, a system based on a pair of leucine zipper domains (see Moll et al., Protein Sci 10:649-655(2001)) that feature complementary charged residues to inhibit homodimerization by electrostatic repulsion and favor heterodimerization by electrostatic attraction is used. (See FIG. 1A, Z1, SEQ ID NO: 2 and Z2, SEQ ID NO: 4).

Figure 8:
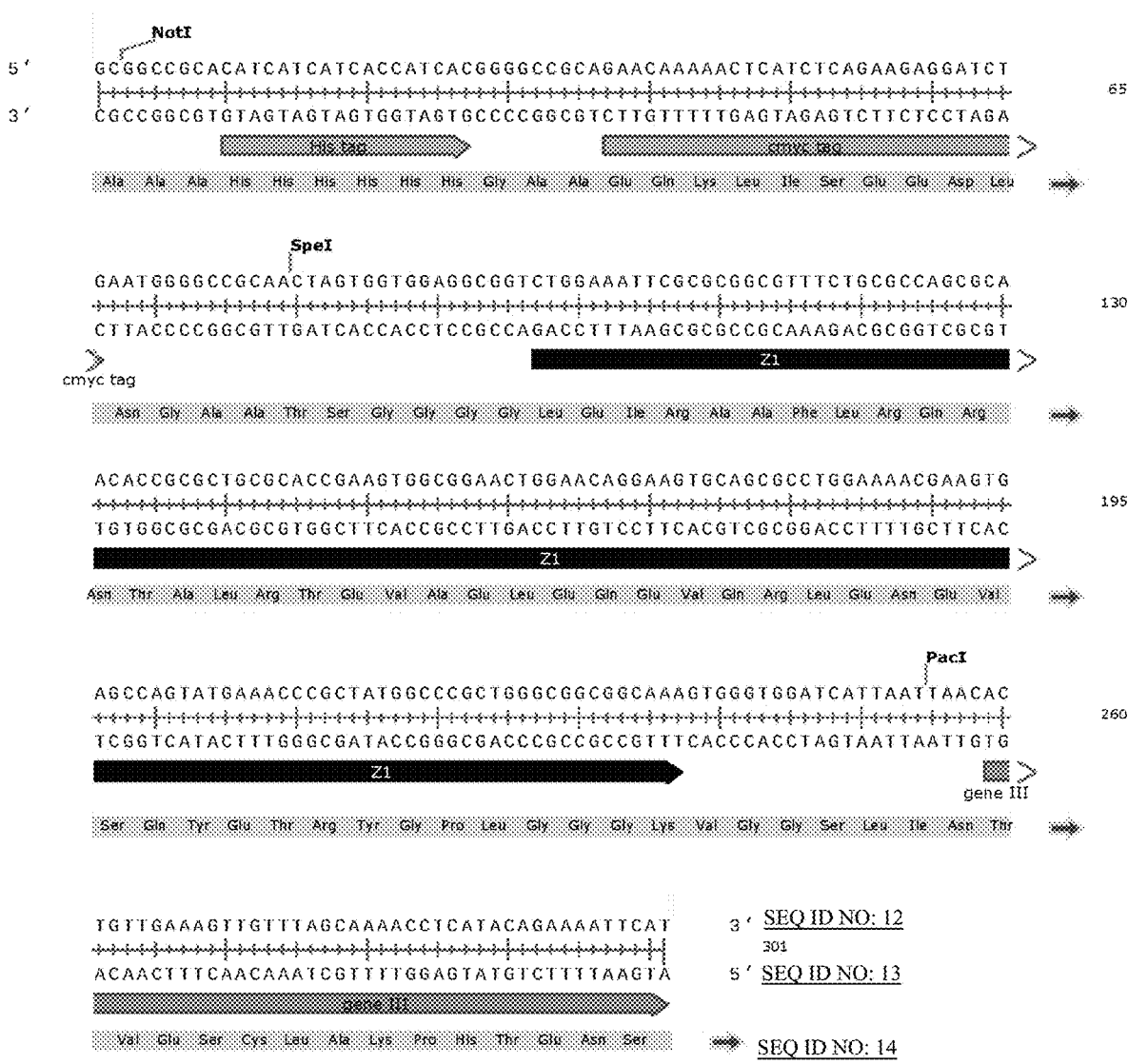
FIG. 8 shows the sequence modifications made to pNDS to generate pNDS-DD. The version encoding leucine zipper domain Z1 (SEQ ID NO: 1) is provided herein as an example, with the sequence of the phagemid from the upstream NotI site to the region encoding the N-terminal residues of the M13 gene 3 protein (SEQ ID NOs: 12, 13 and 14).
Figure 9A:
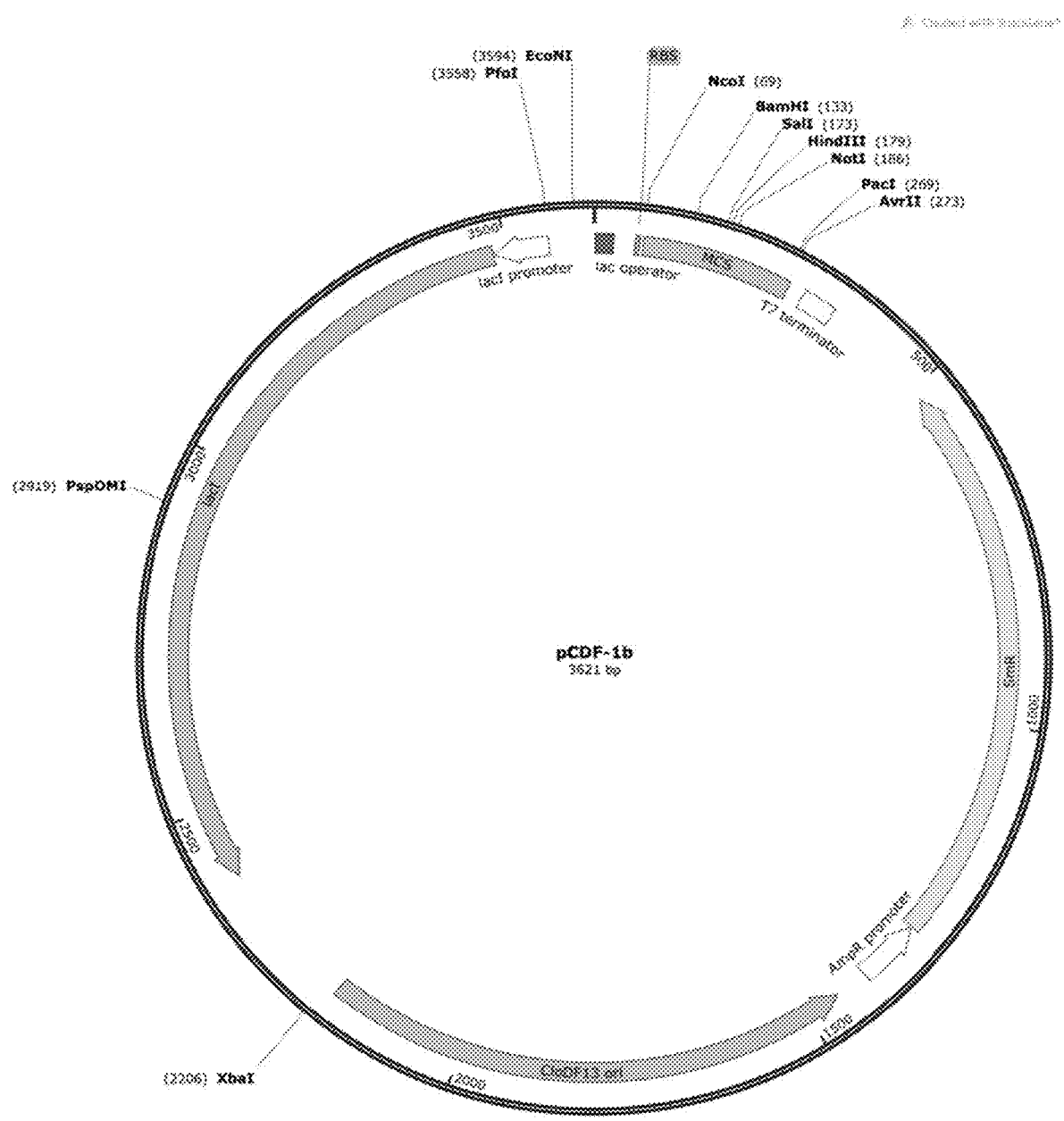
FIG. 9A shows maps of the starting plasmid, pCDF-1b.
Figure 9B:
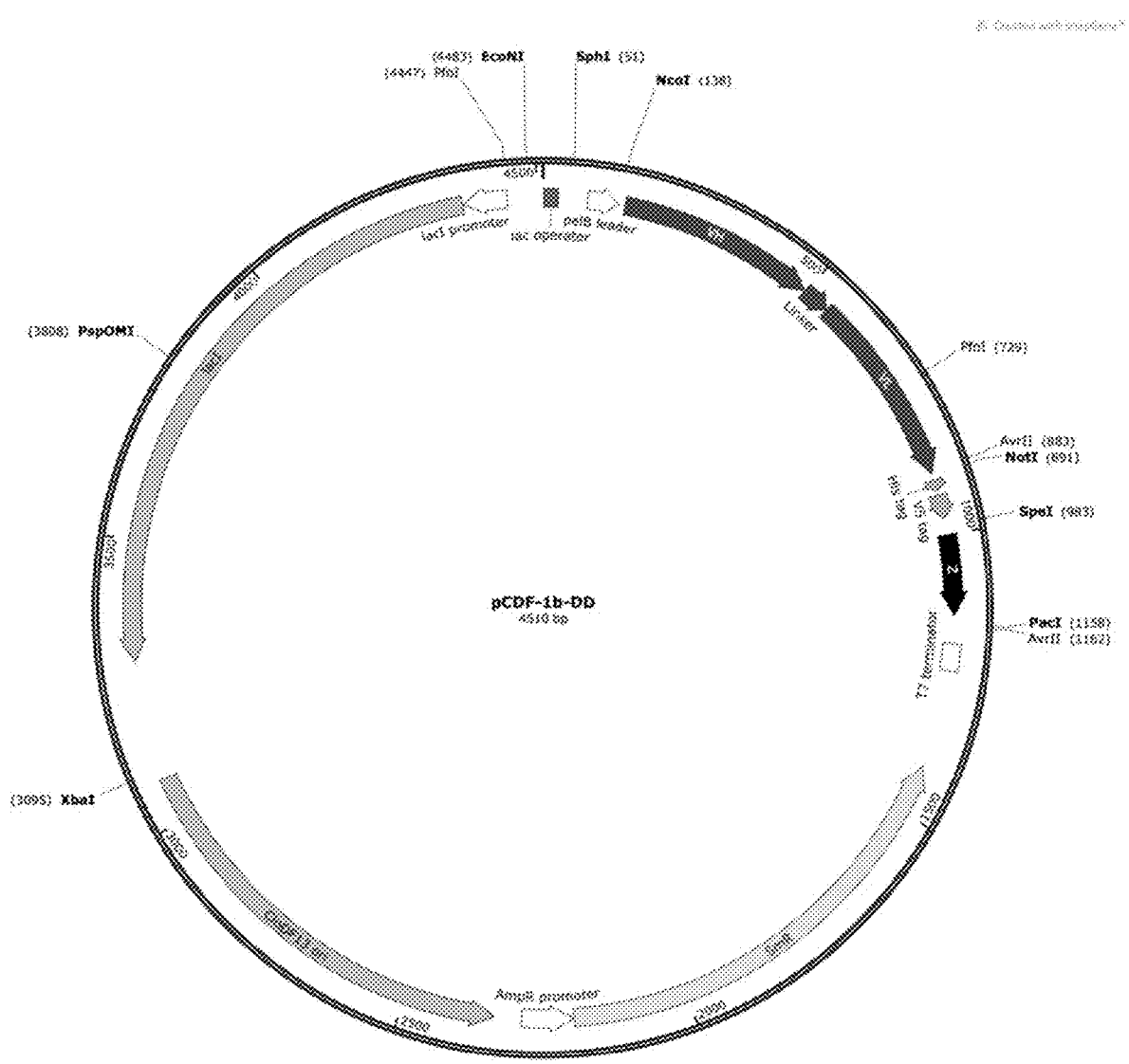
FIG. 9B shows the final phagemid pcDF-1b-DD selected restriction sites and key features.
Figure 10B:
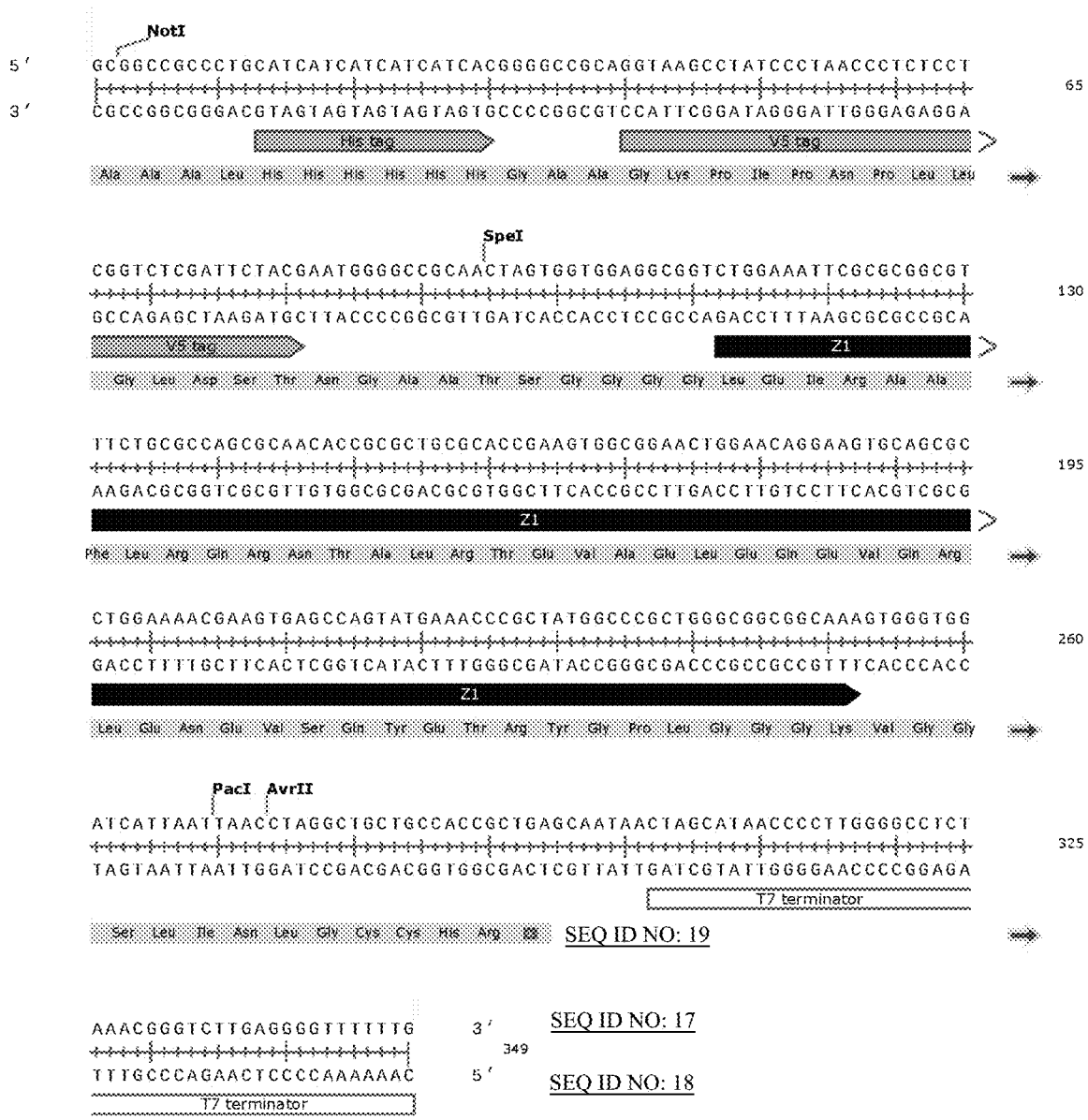
In FIG. 10B, the sequence from pCDF-1b-DD from the NotI site located downstream of encoded scFv fragments to the PacI site on the pCDF-1b backbone with the version encoding leucine zipper domain Z1 provided herein as an example (SEQ ID Nos: 17, 18 and 19).

In this system, one leucine zipper domain is inserted between a first scFv fragment and the phage pIII minor coat protein on a phagemid vector (pNDS-DD) so that both the gene and its product are incorporated into phage particles during rescue (subsequently referred to as the "phage component") (FIG. 8, SEQ ID NOs: 12, 13 and 14). The other leucine zipper domain is appended to a second scFv fragment that is encoded for expression as a soluble periplasmic protein (subsequently referred to as the "soluble component") on a complementary expression vector (pCDF-1b-DD) (FIGS. 9A, 9B, 10A and 10B; SEQ ID NOs: 15, 16, 17, 18 and 19).

During phage assembly and extrusion, the soluble component forms a stable leucine zipper-mediated complex with the phage component in the bacterial periplasm resulting in phage particles displaying two different antibody fragments: the phage component scFv encoded on the packaged phagemid vector plus the soluble component scFv encoded on the plasmid harbored by the bacterial host in which phage rescue is performed. (See FIG. 1B).

The association of the soluble component antibody during phage assembly is dependent on leucine zipper heterodimerization, (see FIG. 2), which drives the selection of rare (i.e. present at 1 in $10^5$ in the initial population) heterodimerization-competent phage clones through several rounds of panning against the target of the soluble component antibody. (See FIG. 3 and Table 1).

TABLE 1

Acquisition by dual display phage of the soluble component antibody is sufficient to drive selection over several rounds of panning and amplification.

| Frequency according to | | Panning on CD3 peptide | | No panning | |
|---|---|---|---|---|---|
| colony sequencing | | Z1 | Z2 | Z1 | Z2 |
| starting ratio | R1 | 0/16 | 16/16 | 19/21 | 2/21 |
| (Z2:Z1) 1:10 | R2 | 0/18 | 18/18 | 11/15 | 4/15 |
| | R3 | 0/17 | 17/17 | 11/16 | 5/16 |
| starting ratio | R1 | 5/6 | 1/6 | 18/18 | 0/18 |
| (Z2:Z1) 1:1000 | R2 | 2/24 | 22/24 | 13/13 | 0/13 |
| | R3 | 0/19 | 19/19 | 22/22 | 0/22 |
| starting ratio | R1 | 12/12 | 0/12 | 10/10 | 0/10 |
| (Z2:Z1) 1:100000 | R2 | 7/14 | 7/14 | 23/23 | 0/23 |
| | R3 | 1/23 | 22/23 | 18/18 | 0/18 |

Characterization of Dual Display Phage

Three antibody fragments of known specificity were used to test the feasibility of dual display: anti-CXCL10 (see Fagete et al., 1:288-296 (2009)), anti-interferon gamma (anti-IFNγ) (See Ravn, et al., 2010) and anti-CD3 peptide (see WO2011/121110). In a first experiment, four pNDS-DD phagemid constructs encoding anti-IFNγ-Z1, anti-IFNγ-Z2, anti-CXCL10-Z1 or anti-CXCL10-Z2 were used for the expression of phage components. These phagemids were rescued in E. coli harboring pCDF-1b-DD plasmids encoding either anti-CD3-Z1 or anti-CD3-Z2 as soluble components. The eight different phage rescue mixtures were assessed by ELISA for their capacity to bind to an immobilized CD3 peptide-Fc fusion protein. (See FIG. 2).

Figure 2:
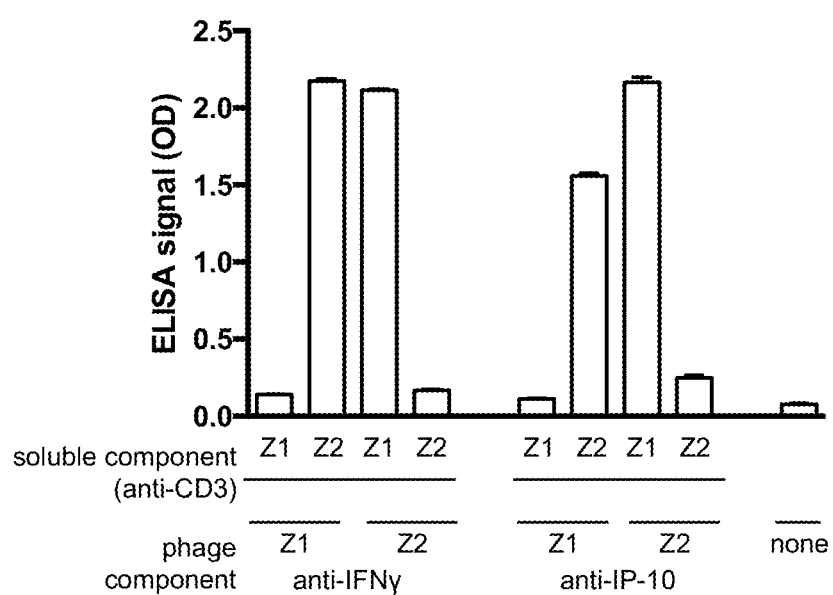
FIG. 2 shows binding activity of various dual display phage constructs produced in E. coli expressing an anti-CD3 soluble component scFv. Phagemids carrying the indicated phage components were rescued in E. coli harboring plasmids encoding either anti-CD3-Z1 or anti-CD3-Z2 as soluble components, and the rescued phage were tested by ELISA for their capacity to bind to immobilized CD3 peptide. Bars represent mean and range of duplicate measurements.

Importantly, positive ELISA signals were only obtained when the soluble component leucine zipper domain was complementary to the leucine zipper domain on the phage component (i.e., Z1 on the phage component, Z2 on the soluble component or vice versa; see FIG. 2), confirming that incorporation of the soluble antibody fragment for dual display is driven by heterodimerization of complementary leucine zipper domains.

Figure 4A:
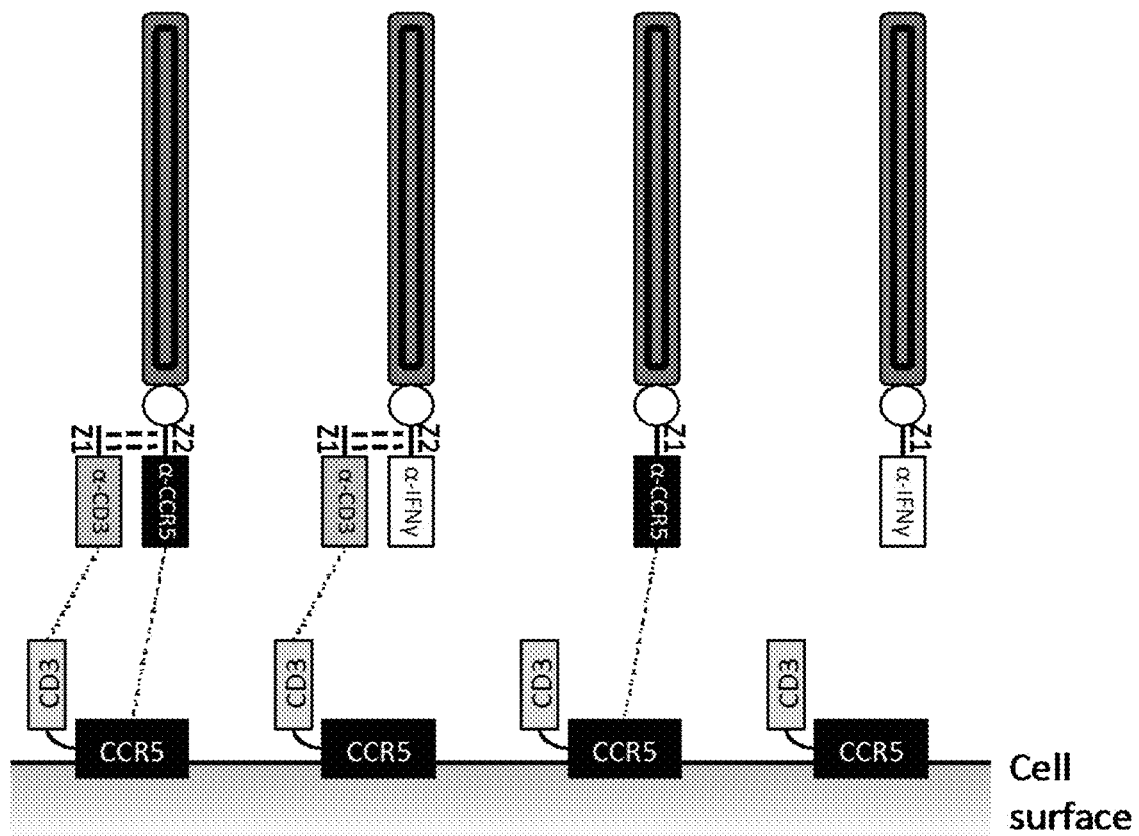
FIGS. 4A-B show the selection strategy based on the capacity of dual display phage to engage two different target structures.

Rare clones (1 in $10^5$) capable of displaying two different antibody specificities can be isolated over several rounds of selection based on their ability to co-engage two user-defined targets (see FIG. 4 and Table 2), thereby providing an important initial proof of concept for the dual display system.

TABLE 2

Dual display selection enriches rare phage clones capable of displaying two different cognate antibodies

| | Antibodies displayed | | Starting propor- | Colonies detected | |
|---|---|---|---|---|---|
| Phage clone | anti-CCR5 | anti-CD3 | tion | Round 3 | Round 4 |
| Anti-CCR5-Z2 | + | + | 1 | 49 | 21 |
| Anti-CCR5-Z1 | + | − | 1 | 0 | 0 |
| Anti-IFNγ-Z2 | − | + | 1 | 2 | 0 |
| Anti-IFNγ-Z1 | − | − | 10000 | 20 | 0 |

Incorporation of the Soluble Component Antibody is Sufficient to Drive Phage Selection To determine whether leucine zipper-mediated acquisition of the soluble component scFv during phage assembly is sufficiently robust to drive phage selection during cycles of panning against its target. pNDS-DD phagemids, encoding either anti-IFNγ-Z1 or anti-IFNγ-Z2 as the phage component, were rescued in E. coli harboring pCDF-1b-DD encoding the anti-CD3-Z1 soluble component. In this way, only the anti-IFNγ-Z2 phage would be capable of acquiring the anti-CD3 scFv through leucine zipper heterodimerization. (See FIG. 3A). This mixture of phage was subjected to rounds of selection panning against immobilized CD3 peptide-Fc fusion protein in order to determine the extent to which anti-CD3-displaying anti-IFNγ-Z2 phage could be enriched from a background of anti-CD3 negative anti-IFNγ-Z1 phage. To control for any enrichment occurring because of possible growth advantage differences between anti-IFNγ-Z1 and anti-IFNγ-Z2 phage, a parallel selection experiment in which rounds of infection and amplification were performed without the CD3 peptide panning step was performed.

Figure 3A:
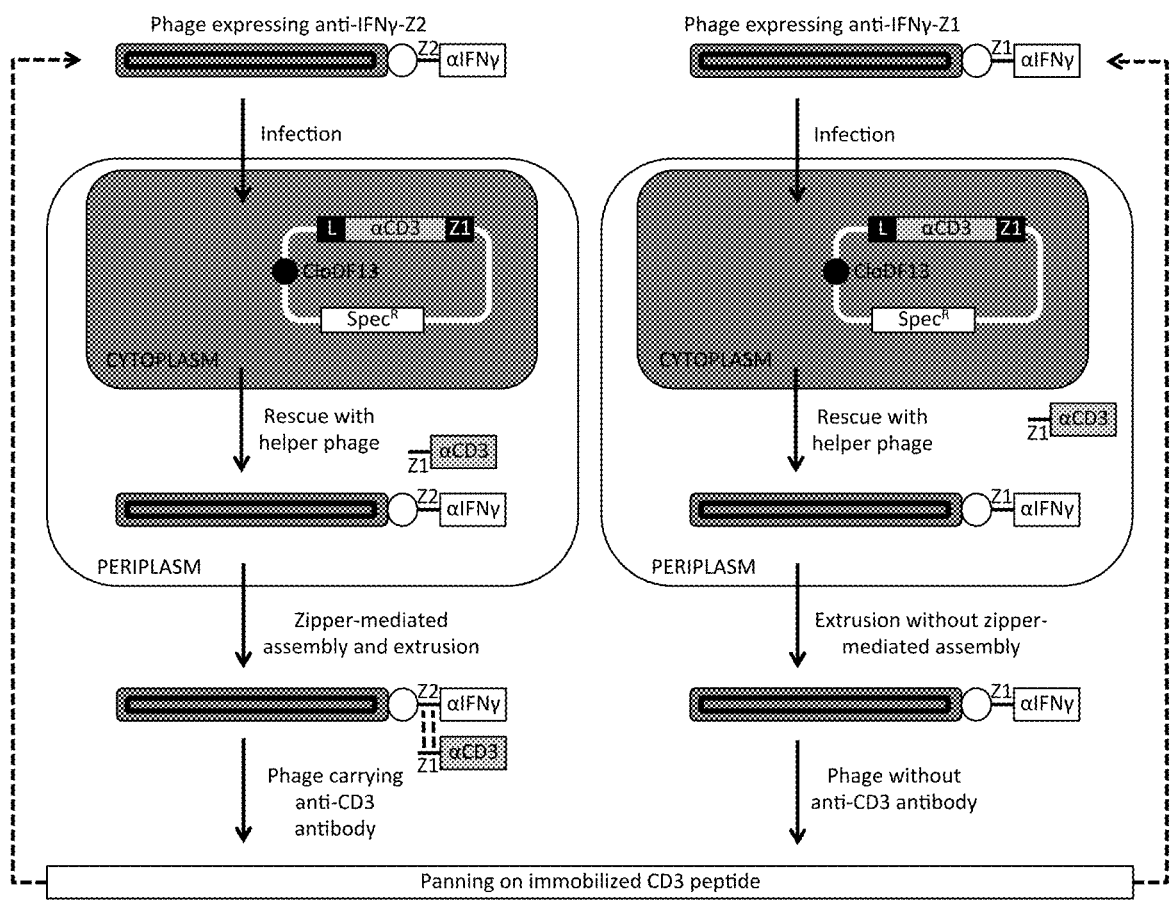
FIGS. 3A-C show that phage selection is driven by the incorporated soluble component antibody.
Figure 3B:
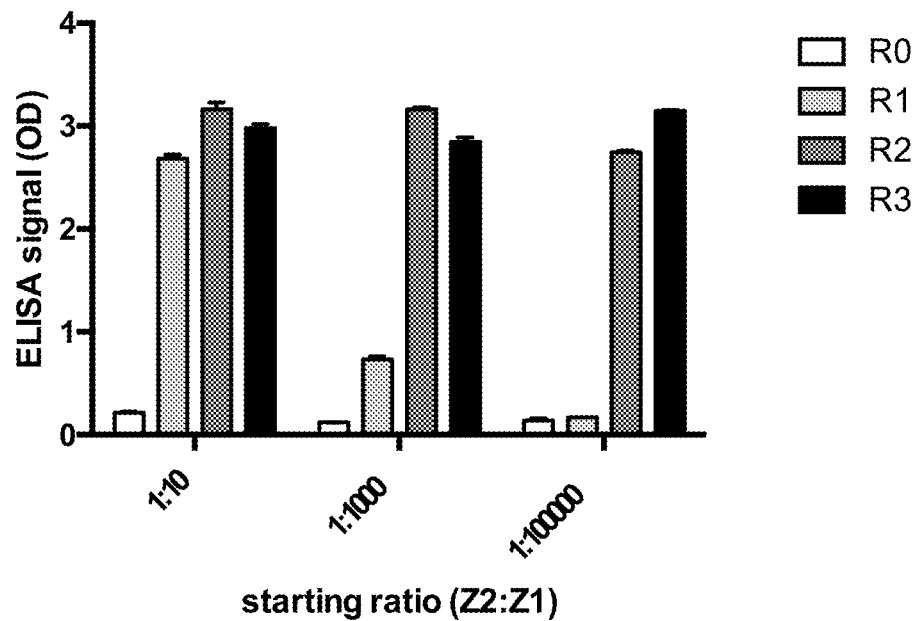
Figure 3C:
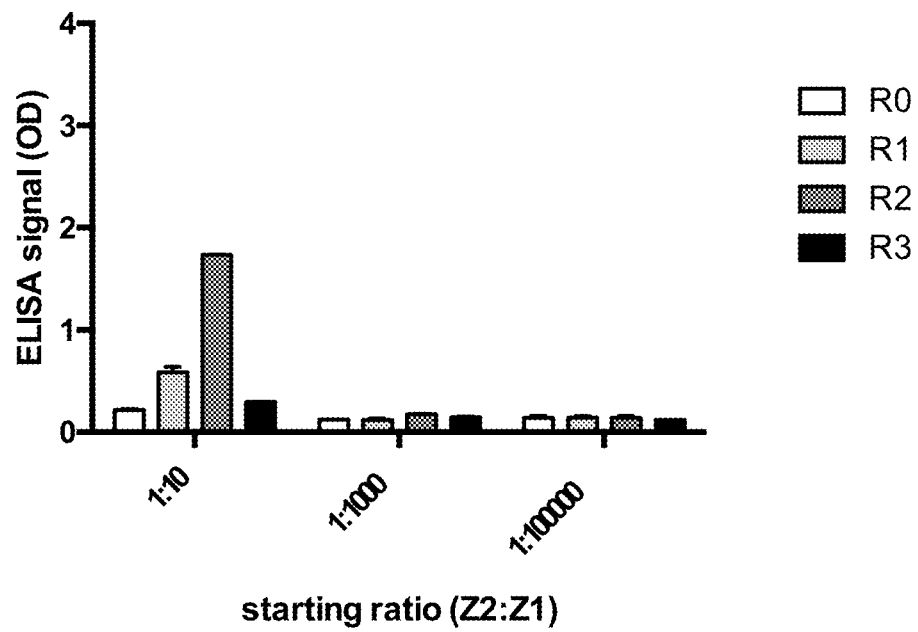

After each round of selection, individual colonies for each phage population were sequenced to determine the proportion of anti-IFNγ-Z2 phage with respect to anti-IFNγ-Z1 (see Table 1), and assessed by ELISA for binding to immobilized CD3 peptide-Fc fusion protein (see FIGS. 3B and 3C). Phage encoding IFNγ-Z2 were mixed with phage encoding IFNγ-Z1 at the indicated ratio, and the mixtures were subjected to rounds of selection as shown in FIG. 3A. Colonies corresponding to individual phage clones were picked at random after each round of selection and sequenced to determine if they corresponded to IFNγ-Z1 or IFNγ-Z2. The anti-IFNγ-Z2 phage, which are capable of acquiring the anti-CD3-Z1 soluble component antibody through leucine zipper heterodimerization, were efficiently enriched during panning against the immobilized CD3 peptide. (See Table 1). As expected, the enrichment was accompanied by increased anti-CD3 phage ELISA signals. (See FIG. 3B). No increase in either Z2 leucine zipper prevalence or anti-CD3 peptide ELISA signal were noted when phage were subjected to rounds of selection in the absence of panning. (See FIG. 3C). Hence, association of the soluble component antibody in the dual display system is sufficiently robust to drive selection over several rounds of panning.

Figure 6:
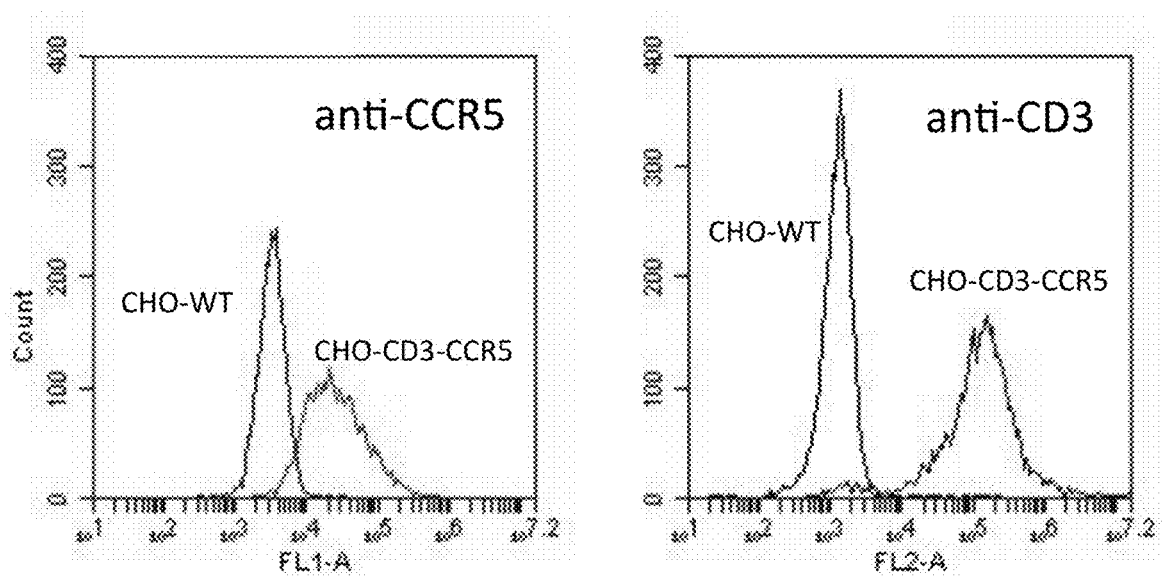
FIG. 6 show the characterization of the CHO-CD3-CCR5 cell line used. Untransfected CHO cells (CHO-WT) or CHO-CD3-CCR5 cells were incubated with antibodies specific for either CCR5 or the CD3 peptide epitope as indicated and analyzed by flow cytometry.

Selection Driven by Co-Engagement of a Two Targets with the Two Displayed Antibodies Selection of dual display phage can be driven by co-engagement of two different target epitopes. For example, a clonal cell line (CHO-CD3-CCR5) was generated stably expressing a cell surface receptor, CCR5, with the CD3 epsilon (1-15) peptide appended to its extracellular N-terminal domain. (See FIG. 4A and FIG. 6A). Having reformatted a well characterized anti-CCR5 antibody, (PRO-140) (see Trkola et al., J. Virol. 75:579-588 (2001)) as a scFv fragment, the cell line was used in a selection experiment involving phage clones encoding four different phage components: anti-CCR5-Z1, anti-CCR5-Z2, anti-IFNγ-Z1 and anti-IFNγ-Z2.

After rescue in E. coli expressing anti-CD3-Z1 soluble component, each of the four phage clones would be expected to display a different combination of antibodies: anti-CCR5-Z2 phage with both anti-CCR5 and anti-CD3 antibodies, anti-CCR5-Z1 phage with anti-CCR5 only, anti-IFNγ-Z2 phage with anti-CD3 only, and anti-IFNγ-Z1 with neither cognate antibody. (See FIG. 4A). The cognate phage clones (anti-CCR5-Z2, anti-CCR5-Z1 and anti-IFNγ-Z2) were each diluted ten-thousand-fold with respect to the non-cognate clone (anti-IFNγ-Z1) and subjected to rounds of panning on CHO-CD3-CCR5 cells. (See FIG. 4B).

Analysis of enrichment was carried out by sequencing randomly picked colonies after selection rounds 3 and 4. (See Table 2). Four different phage clones capable of displaying different combinations of cognate antibodies (see FIG. 4A) were mixed to provide the indicated starting proportions. After Round 3 and Round 4 of selection, colonies corresponding to individual phage clones were picked at random and sequenced. The number of colonies identified as corresponding to each phage clone is indicated. As expected, the non-cognate phage clone (anti-IFNγ-Z1), which was initially present at a ten thousand-fold excess, was progressively eliminated during. Importantly, of the phage clones displaying one or more cognate antibodies, only the clone displaying both anti-CD3 and anti-CCR5 (anti-CCR5-Z2) was enriched during selection: anti-CCR5-Z2 was the only one of the four starting clones that was detectable after round 4. Hence, dual display can be used to specifically enrich rare phage (i.e. present at 1 in $10^5$ in the initial population) capable of displaying antibodies against two different target structures.

Adapting Dual Display for Library-Based Selection

The dual replicon strategy described herein was designed to make the dual display system readily amenable to library-based selection. A "single pot" dual display naive antibody library could be cloned into the pNDS-DD phagemid and then used with different user-defined soluble component antibodies: requiring a new bacterial strain harboring the soluble component antibody fragment of choice to be generated, infected by the dual display naive antibody library and then subjected to rescue by helper phage.

Enabling Co-Selection of Functional Ligand Pairs

In one embodiment, where one target antibody specificity the (soluble component) must be fixed by the user prior to each selection experiment, combinatorial screening to search for novel pairs of compatible antibodies is not possible. However, this system could be adapted to allow direct selection of functional pairs of antibodies, by making use of the LoxP/Cre combinatorial infection/in vivo recombination system. (See Waterhouse et al., Nucleic Acids Res. 21:2265-2266 (1993)). In this process, bacteria are transformed with a donor plasmid library, and then infected with phage capable of acquiring sequences from the donor plasmid by recombination. Combinatorial dual display phagemid libraries encoding both soluble and phage component antibodies could be generated by adapting the pNDS-DD and pCDF-1b-DD vectors to include appropriate flanking recombination sites.

Accordingly, any of the systems and methods described herein could be used for direct isolation of pairs of antibodies capable of co-engaging two different cell surface markers (e.g., on tumor cells) to increase target cell specificity. Additionally (or alternatively), pairs of antibodies capable of inducing heterodimerization of two different target cell receptors could be used to fine tune modulation of cell signaling activity.

EXAMPLES

Example 1: Antibody Dual Display: A Method of Streamline the Discovery of Bispecific Antibodies Plasmids, Phagemids, Helper Phage and Bacterial Strains The plasmids pCDNA3.1 and pCDF-1b were purchased from Invitrogen and Novagen, respectively. The phagemid vector pNDS has been described previously (see Venet et al., PLoS One 7:e43471 (2012)). Helper phage M13KO7 (see Vieira et al., Methods Enzymol. 153:3-11(1987)) and E. coli TG1 (K-12 supE thi-1 Δ(lac-proAB) Δ(mcrB-hsdSM)5, (rκmκ) F' [traD36 proAB⁺ lacI^q lacZΔM15]) were produced internally. E. coli XL1-Blue (recA1 endA1 gyrA96 thi-1 hsdR17 supE44 relA1 lac) was purchased from Agilent Technologies.

Antibodies, Cell Lines and Materials

Antibodies.

Anti-human CXCL10 (see Fagete et al., 1:288-296 (2009)) and anti-human IFNγ (see Ravn et al., Nucleic Acids Res. 38:e193(2010)) antibodies were isolated from naïve scFv phage display libraries using standard phage display selection and screening procedures. Genes encoding VH and VL domains of previously described antibodies directed against human CCR5 (see Trkola et al., J. Virol. 75:579-588(2001)) and residues 1-15 of the mature form of the human CD3 epsilon subunit (see WO2011/121110) were synthesized (Eurofins) and assembled as scFv fragments.

CHO-CD3-CCR5 Cells.

Figure 5:
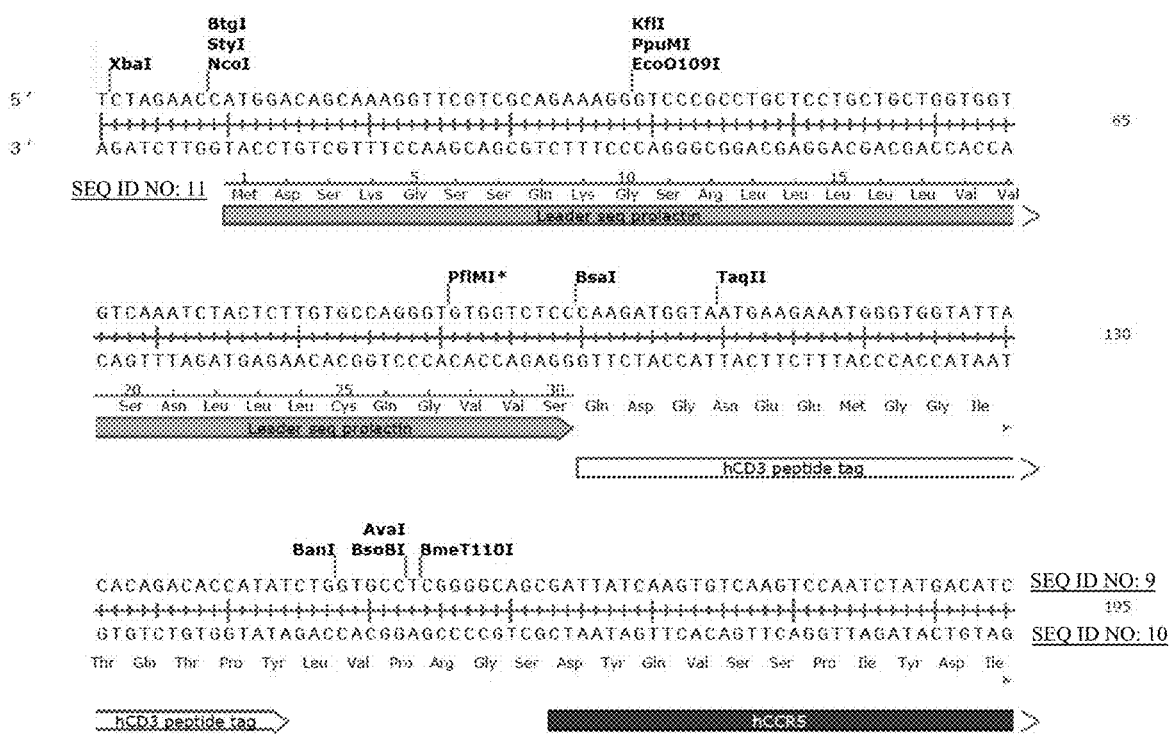
FIG. 5 shows the sequence of the pcDNA3.1 vector encoding a CD3 epitope tag N-terminally fused to human CCR5 and the sequence from the XbaI cloning site on the pcDNA3.1 backbone to the region encoding the N-terminal residues of CCR5 (SEQ ID NOs: 9, 10 and 11).

A fusion construct encoding human CCR5 preceded by the human prolactin leader sequence and 1-15 of the mature form of the human CD3 epsilon subunit was cloned into the mammalian cell expression vector pCDNA3.1. The resulting plasmid was used to transfect Chinese Hamster Ovary (CHO) cells, which were then amplified in the presence of the selection antibiotic G418 (Invitrogen, 1.2 mg/mL). Individual clones were isolated by cell sorting followed by further expansion, with a single clone chosen based on flow cytometry analysis of surface expression of both CCR5 and the CD3 epsilon subunit peptide epitope. Construction of expression vector. The gene coding for the mature protein human CCR5 (NCBI reference NM 000579) was assembled by PCR extension to N-terminally append (i) the bovine prolactin precursor leader sequence (NCBI reference NM_173953), (ii) residues 1-15 of the mature human CD3 epsilon subunit (NCBI reference NM_000733.3) (See FIG. 5 below; and SEQ ID NOs: 9, 10 and 11). The resulting fragment was cloned into the mammalian cell expression vector pcDNA3.1 (Invitrogen) using XbaI and NotI restriction sites.

Biotinylated CD3 Peptide-Fc.

PCR extension was used to fuse the sequence encoding residues 1-15 of human CD3 epsilon to the N-terminus of the human yl Fc region and incorporate a C-terminal Avi-Tag™ sequence (Avidity). This fragment was cloned into the Peak8 mammalian expression vector (Edge Biosystems) using HindIII and EcoRI sites, and the fusion protein was expressed as described previously. (See Magistrelli et al., Protein Expr. Purif. 72:209-216(2010)). After 10 days production in a CELLine bioreactor (Integra), the harvested protein was purified on a protein G Sepharose column (GE healthcare) using an AKTA Prime chromatography system (Amersham Pharmacia Biotech). The purified protein was biotinylated in vitro by using BirA enzyme (Avidity) according to the manufacturer's instructions, desalted using a PD10 column (GE healthcare), and verified for purity and integrity by SDS-PAGE.

Dual Replicon System Molecular Cloning
Dual Display Phagemid (pNDS-DD).

The phagemid pNDS was modified using a QuikChange cloning strategy (Agilent Technologies) to introduce SpeI and PacI sites in frame with the phage gene 3 coding sequence and remove the amber codon. The SpeI and PacI sites were then used to insert fragments corresponding to *E. coli* codon-optimized coding sequences corresponding to Z1 and Z2 leucine zipper domains (see Moll et al., Protein Sci 10:649-655(2001)) and flanked by glycine/serine-rich spacers. Antibody scFv fragments were then cloned into dual display phagemids using the standard SfiI and NotI sites in the phagemid backbone.

Generation and Characterization of Stably Transfected Clonal Cell Line.

The resulting plasmid was transfected into Chinese Hamster Ovary cells using Lipofectamine™ (ThermoFisher) according to the manufacturer's instructions. Stably transfected cells were selected by culture in the presence of 1.2 mg/mL geneticin (ThermoFisher), and individual clones were isolated by cell sorting. Clonal cell lines were assessed by flow cytometry using an anti-CCR5 antibody (HEK/1/85a mAb directly conjugated to Alexa Fluor 488, BioLegend) and an anti-CD3 peptide antibody (see Pande et al., 28:849-858(2010)) (assembled for expression as an intact human immunoglobulin) used with phycoerythrin-conjugated mouse anti-human Fc secondary antibody (Clone H2, Southern Biotech).

Plasmid for Soluble Component Expression (pCDF-1b-DD).

Figure 7A:
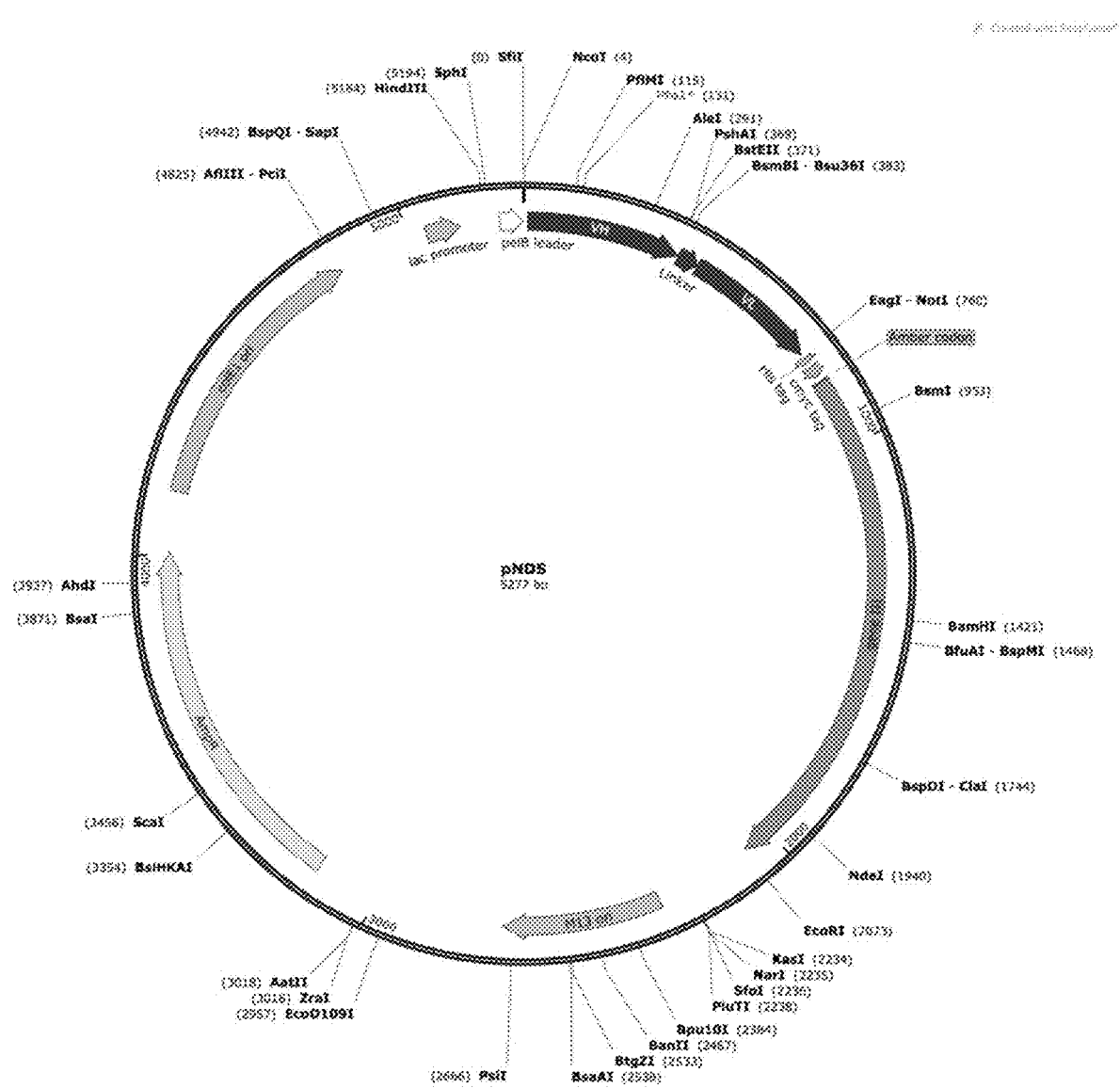
FIG. 7A shows maps of the starting phagemid, pNDS.
Figure 7B:
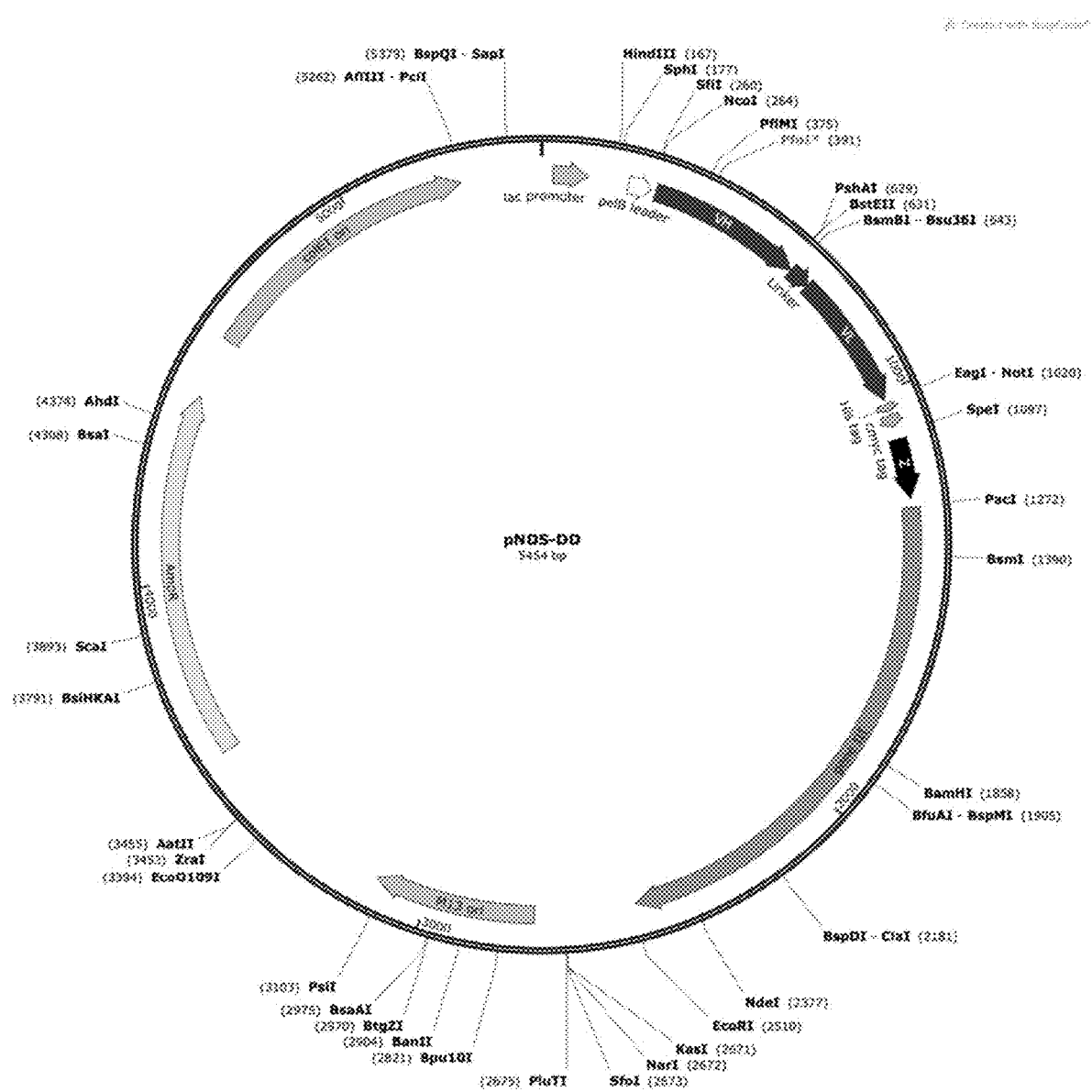
FIG. 7B, shows the final phagemid pNDS-DD unique restriction sites and key features.

A SphI restriction site was inserted upstream of the multiple cloning site of pCDF-1b using QuikChange mutagenesis (Agilent Technologies). This site, together with the PacI site in the plasmid backbone, was used to insert SphI-PacI fragments from donor phagemid vectors corresponding to the encoded scFv-leucine zipper fusion proteins. The steps taken to modify the starting phagemid, pNDS, in order to generate the final phagemid, pNDS-DD are shown in FIGS. 7A and 7B.

Phage Rescue pNDS-DD Phagemids introduced into *E. coli* TG1 harboring pCDF-1b-DD plasmids were rescued using M13KO7 helper phage according to standard procedures (See Hoogenboom et al., Nucleic Acids Res. (1991) 19, 4133-4137.), except that spectinomycin (30 µg/mL), the selection antibiotic on the pCDF-1b-DD plasmid, was used in addition to ampicillin (100 µg/mL) and kanamycin (50 µg/mL). Rescued phage were precipitated twice by incubating rescue supernatant for 2 h at 4° C. with a volume of polyethylene glycol 8000 (20% (w/v), Acros Organics)/2.5 M NaCl solution corresponding to 30% of the rescue supernatant volume. Precipitates were then resuspended in 10 mM Tris-HCL buffer (pH 8.0) supplemented with 1 mM EDTA (Tris-EDTA buffer).

Phage ELISA

Maxisorp plates (Nunc) were coated (4° C., overnight) with 1 µg/mL streptavidin (Roche), then washed with PBS supplemented with 0.05% Tween 20 (PBS-Tween 0.05%) and blocked with PBS supplemented with 3% (w/v) milk powder (Sigma) (PBS-milk). Plates were then incubated at ambient temperature for 1 h with biotinylated CD3 peptide-Fc (1 µg/mL), then washed with PBS-Tween 0.05% and incubated (ambient temperature, 1 h) with rescued phage suspended in PBS-milk. After washing with PBS-Tween 0.05%, plates were incubated at ambient temperature for 1 h with horseradish peroxidase-conjugated anti-M13 antibody (1:5000, Amersham). Plates were washed again with PBS-Tween 0.05% and revealed using TMB substrate (Sigma-Aldrich), with the reaction stopped after 20 min with 1 M H2SO4 prior to absorbance measurement at 450 nm.

Panning Selection Against Immobilized CD3 Peptide

Phage mixtures ($10^{12}$ cfu) were suspended in 1 mL PBS-milk and pre-adsorbed (ambient temperature, 1 h) on streptavidin magnetic beads (Dynal M-280). A separate batch of streptavidin magnetic beads (100 µL) was blocked with PBS-milk for 1 h at ambient temperature and coated with biotinylated CD3 peptide-Fc (100 nM, ambient temperature, 1 h). Beads were then washed first with 1 mL PBS supplemented with 0.1% Tween 20 (PBS-Tween 0.1%), then with 1 mL PBS and finally with 1 mL PBS-milk prior to incubation (ambient temperature, 2 h) with the pre-adsorbed phage. The beads were then washed with PBS-Tween 0.1% (five times) followed by PBS (twice) and then incubated for one hour at 37° C. with exponentially growing *E. coli* TG1. The bacterial culture was then spread on to plates containing 2×TY agar supplemented with ampicillin and glucose.

Co-Engagement Selections

Figure 4B:
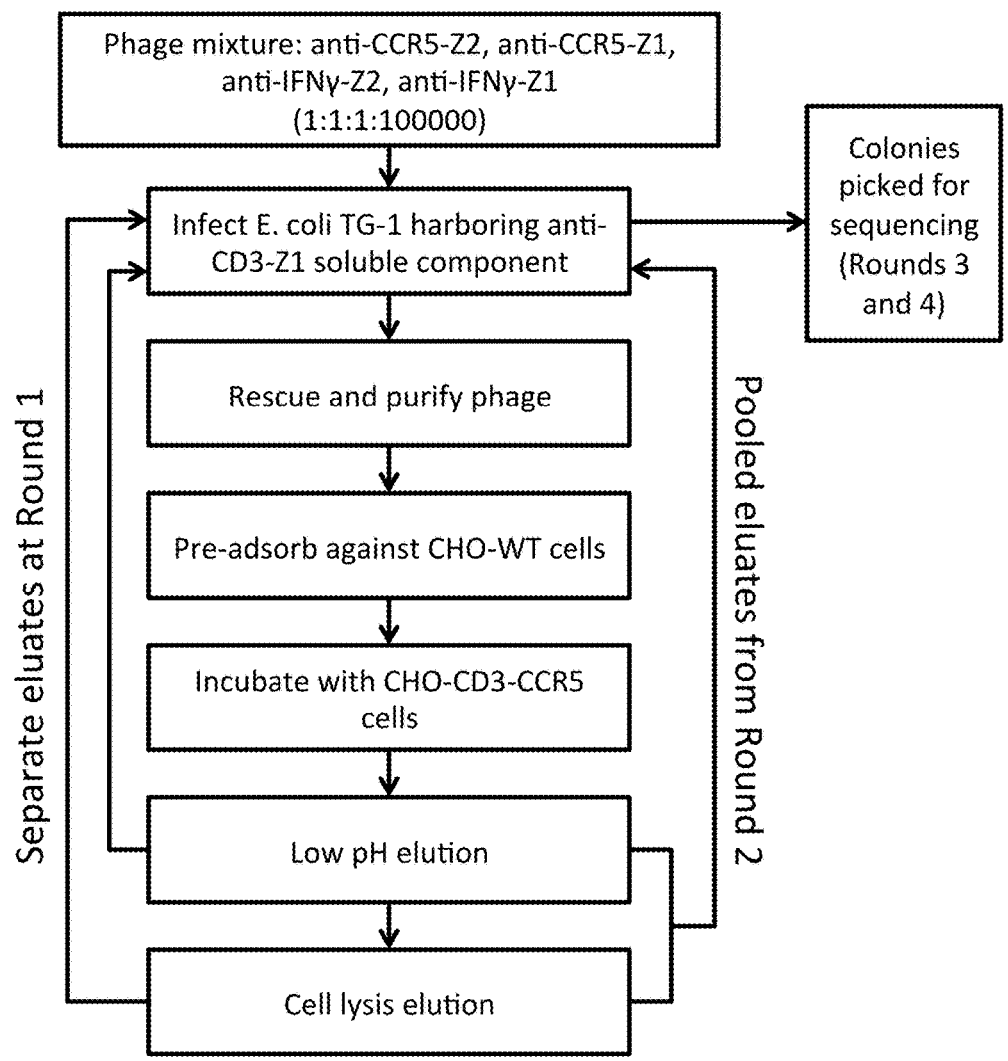

This procedure is shown schematically represented in FIG. 4B.

Blocking Phage.

Phage mixtures (approx. $10^{11}$ cfu for the first round, then $10^9$-$10^{10}$ cfu for subsequent rounds) were blocked in 300 µL PBS supplemented with bovine serum albumin (3% (w/v) Sigma) at ambient temperature for 1 h on a rotary shaker (20 rpm).

Pre-Adsorption on Untransfected CHO Cells.

The blocked phage mixture was used to resuspend $10^7$ untransfected CHO cells, with the resulting suspension kept on ice for 1 h. The suspension was then centrifuged at 300 g (4° C., 3 min), and the supernatant containing cell-free phage was recovered.

Incubation with Cho-Cd3-Ccr5 Cells.

The recovered supernatant was used to resuspend $10^7$ CHO CCR5-CD3 cells, with the resulting suspension was incubated at 4° C. for 2 h on a rotary shaker (10 rpm) then washed with 1 mL ice cold PBS-Tween 0.05% (four times) followed by 1 mL ice cold PBS (twice).

Low pH Elution.

The cell suspension was centrifuged at 300 g (4° C., 3 min), then resuspended in 500 µL Glycine HCl buffer (0.2 M pH 2.2) and left for 10 min on ice prior to neutralization with Tris-EDTA buffer. It was again centrifuged (300 g, 4° C., 3 min), with both the supernatant containing acid-eluted phage and the cell pellet recovered separately.

Cell Lysis Elution and Infection of *E. coli*.

Pelleted cells were resuspended in 500 µL Tris-EDTA and lysed using three rapid freeze-thaw cycles. The lysates, either combined with the acid elutions (selection rounds 2 to 4) or used alone (round 1), were added to 10 mL of exponentially growing *E. coli* TG1 cells and incubated at 37° C., for 1 h. The resulting bacterial culture was spread on plates containing 2×TY agar supplemented with ampicillin and glucose.

Sequencing of Individual Phage Colonies

After each round of selection, unique *E. coli* TG1 colonies harboring individual phage clones were picked and cultured overnight in LB broth supplemented with ampicillin and glucose. Plasmid minipreps were prepared and used for insert sequencing (Microsynth). Analysis of the resulting sequences was used to determine both the scFv and the leucine zipper domain encoded on each phagemid clone.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A display system for simultaneously displaying two ligand binding polypeptides at the surface of a filamentous bacteriophage, comprising:
   a. a phagemid comprising the coding sequence of a first ligand binding polypeptide fused in frame to a first dimerization domain and to minor coat protein 3 of filamentous bacteriophage;
   b. a plasmid comprising the coding sequence of a second ligand binding polypeptide fused in frame to a second dimerization domain;
   wherein the first dimerization domain and the second dimerization domain are leucine zippers that heterodimerize with high affinity, and
   c. a helper phage comprising coding sequences of all proteins necessary for packaging the phage;
   wherein the first and second ligand binding polypeptides are different scFvs and each bind to a different target ligand, and
   wherein, when the first and second ligand binding polypeptide fusions and all phage proteins are expressed in a suitable host cell, the two ligand binding polypeptide fusions associate via their respective dimerization domains, resulting in simultaneous display of the two ligand binding polypeptides at the surface of phage.

2. The display system of claim 1, wherein the first dimerization domain is encoded by the nucleic acid sequence of SEQ ID NO: 1 and the second dimerization domain is encoded by the nucleic acid of SEQ ID NO: 3.

3. The display system of claim 1, wherein the first dimerization domain comprises the amino acid sequence of SEQ ID NO: 2 and the second dimerization domain comprises the amino acid sequence SEQ ID NO: 4.

4. The display system of claim 1, wherein the first dimerization domain is encoded by the nucleic acid sequence of SEQ ID NO: 5 and the second dimerization domain is encoded by the nucleic acid of SEQ ID NO: 7.

5. The display system of claim 1, wherein the first dimerization domain comprises the amino acid sequence of SEQ ID NO: 6 and the second dimerization domain comprises the amino acid sequence SEQ ID NO: 8.

6. The display system of claim 1, wherein, when expressed in the host cell, two ligand binding polypeptides displayed on the surface of the phage have a geometry comparable to that of an IgG molecule.

7. The display system of claim 1, wherein, when expressed in the host cell, the two ligand binding polypeptides displayed on the surface of the phage have a molecular separation distance comparable to that of an IgG molecule.

8. The display system of claim 1, wherein, when expressed in the host cell, the two ligand binding polypeptides displayed on the surface of the phage have both a geometry and molecular separation distance comparable to that of an IgG molecule.

9. A kit comprising the display system of claim 1 in suitable packaging.

10. The kit of claim 9, wherein the kit additionally comprises instructions for use.

11. A method for displaying two ligand polypeptides on the surface of a phage, the method comprising causing the display system of claim 1 to be transcribed and translated into a suitable host cell.

12. A method of detecting a simultaneous specific interaction between one or more test agents and two ligand binding polypeptides displayed on the surface of a phage, the method comprising;
   a. providing a phage displaying the two ligand binding polypeptides that is prepared according to the method of claim 11;
   b. contacts the phage with the one or more test agents under conditions suitable to produce a stable complex between the two ligand binding peptides and the agents; and
   c. detecting the formation of the stable complex.

13. The method of claim 12, wherein the one or more test agent is selected from the group consisting of protein, polysaccharide, lipid, and combinations thereof.

14. The method of claim 13, wherein the one or more test agent are antigens or ligands.

15. A method of screening ligand polypeptide pairs for co-selecting functional ligand polypeptide pairs that co-engage one of more targets, the method comprising:
   a) providing a plurality of the dual display system of claim 1, wherein each dual display system comprises the coding sequences of a first and a second ligand binding polypeptides of any one of the ligand polypeptide pairs to be screened;
   b) producing a set of phage populations displaying the ligand polypeptide pairs of a) using a method for displaying two ligand polypeptides on the surface of a phage, the method comprising causing the display system of claim 1 to be transcribed and translated into a suitable host cell, wherein each phage population displays a ligand polypeptide pair that is different from the ligand polypeptide pair displayed by another phage population in the set;
   d) contacting each phage population of b) with the one or more targets under conditions suitable to produce a stable complex between the two ligand binding peptides of a ligand polypeptide pair and the one or more targets; and
   e) detecting the one or more ligand polypeptide pair of d) that form a stable complex with the one or more targets;
   f) selecting the ligand polypeptide pair of the one or more dual display system of e) as functional ligand polypeptide pairs that co-engage the one of more targets.

16. The method of claim 15, wherein the one or more target is selected from the group consisting of protein, polysaccharide, lipid, and combinations thereof.

17. The method of claim 16, wherein the one or more target are antigens or ligands.

* * * * *

SEQUENCE LISTING

```
<160> NUMBER OF SEQ ID NOS: 19

<210> SEQ ID NO 1
<211> LENGTH: 141
<212> TYPE: DNA
<213> ORGANISM: Artificial Sequence
<220> FEATURE:
<223> OTHER INFORMATION: Artificial Polynucleotide

<400> SEQUENCE: 1
ctggaaattc gcgcggcgtt tctgcgccag cgcaacaccg cgctgcgcac cgaagtggcg      60
gaactggaac aggaagtgca gcgcctggaa acgaagtga gccagtatga aacccgctat     120
ggcccgctgg gcggcggcaa a                                               141

<210> SEQ ID NO 2
<211> LENGTH: 47
<212> TYPE: PRT
<213> ORGANISM: Artificial Sequence
<220> FEATURE:
<223> OTHER INFORMATION: Artificial Polypeptide

<400> SEQUENCE: 2

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30

Val Ser Gln Tyr Glu Thr Arg Tyr Gly Pro Leu Gly Gly Gly Lys
        35                  40                  45

<210> SEQ ID NO 3
<211> LENGTH: 141
<212> TYPE: DNA
<213> ORGANISM: Artificial Sequence
<220> FEATURE:
<223> OTHER INFORMATION: Artificial Polynucleotide

<400> SEQUENCE: 3
ctggaaattg aagcggcgtt tctggaacgc gaaaacaccg cgctggaaac ccgcgtggcg      60
gaactgcgcc agcgcgtgca gcgcctgcgc aaccgcgtga gccagtatcg cacccgctat     120
ggcccgctgg gcggcggcaa a                                               141

<210> SEQ ID NO 4
<211> LENGTH: 47
<212> TYPE: PRT
```

<213> ORGANISM: Artificial Sequence
<220> FEATURE:
<223> OTHER INFORMATION: Artificial Polypeptide

<400> SEQUENCE: 4

```
Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
                20                  25                  30

Val Ser Gln Tyr Arg Thr Arg Tyr Gly Pro Leu Gly Gly Lys
            35                  40                  45
```

<210> SEQ ID NO 5
<211> LENGTH: 102
<212> TYPE: DNA
<213> ORGANISM: Homo sapiens

<400> SEQUENCE: 5

```
gaagaaaaaa gccgcctgct ggaaaaagaa aaccgcgaac tggaaaaaat tattgcggaa      60
aaagaagaac gcgtgagcga actgcgccat cagctgcaga gc                        102
```

<210> SEQ ID NO 6
<211> LENGTH: 34
<212> TYPE: PRT
<213> ORGANISM: Homo sapiens

<400> SEQUENCE: 6

```
Glu Glu Lys Ser Arg Leu Leu Glu Lys Glu Asn Arg Glu Leu Glu Lys
1               5                   10                  15

Ile Ile Ala Glu Lys Glu Glu Arg Val Ser Glu Leu Arg His Gln Leu
                20                  25                  30

Gln Ser
```

<210> SEQ ID NO 7
<211> LENGTH: 102
<212> TYPE: DNA
<213> ORGANISM: Homo sapiens

<400> SEQUENCE: 7

```
accagccgcc tggaaggcct gcagagcgaa aaccatcgcc tgcgcatgaa aattaccgaa      60
ctggataaag atctggaaga agtgaccatg cagctgcagg at                        102
```

<210> SEQ ID NO 8
<211> LENGTH: 34
<212> TYPE: PRT
<213> ORGANISM: Homo sapiens

<400> SEQUENCE: 8

```
Thr Ser Arg Leu Glu Gly Leu Gln Ser Glu Asn His Arg Leu Arg Met
1               5                   10                  15

Lys Ile Thr Glu Leu Asp Lys Asp Leu Glu Glu Val Thr Met Gln Leu
                20                  25                  30

Gln Asp
```

<210> SEQ ID NO 9
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 9

```
tctagaacca tggacagcaa aggttcgtcg cagaaagggt cccgcctgct cctgctgctg    60
gtggtgtcaa atctactctt gtgccagggt gtggtctccc aagatggtaa tgaagaaatg   120
ggtggtatta cacagacacc atatctggtg cctcggggca gcgattatca agtgtcaagt   180
ccaatctatg acatc                                                    195
```

<210> SEQ ID NO 10
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 10

```
agatcttggt acctgtcgtt ccaagcagc gtctttccca gggcggacga ggacgacgac     60
caccacagtt tagatgagaa cacggtccca caccagaggg ttctaccatt acttctttac   120
ccaccataat gtgtctgtgg tatagaccac ggagccccgt cgctaatagt tcacagttca   180
ggttagatac tgtag                                                    195
```

<210> SEQ ID NO 11
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 11

```
Met Asp Ser Lys Gly Ser Ser Gln Lys Gly Ser Arg Leu Leu Leu Leu
1               5                   10                  15
Leu Val Val Ser Asn Leu Leu Leu Cys Gln Gly Val Val Ser Gln Asp
            20                  25                  30
Gly Asn Glu Glu Met Gly Gly Ile Thr Gln Thr Pro Tyr Leu Val Pro
        35                  40                  45
Arg Gly Ser Asp Tyr Gln Val Ser Ser Pro Ile Tyr Asp Ile
    50                  55                  60
```

<210> SEQ ID NO 12
<211> LENGTH: 301
<212> TYPE: DNA
<213> ORGANISM: Artificial Sequence
<220> FEATURE:
<223> OTHER INFORMATION: Synthetic Polynucleotide

<400> SEQUENCE: 12

```
gcggccgcac atcatcatca ccatcacggg gccgcagaac aaaaactcat ctcagaagag    60
gatctgaatg gggccgcaac tagtggtgga ggcggtctgg aaattcgcgc ggcgtttctg   120
cgccagcgca acaccgcgct gcgcaccgaa gtggcggaac tggaacagga agtgcagcgc   180
ctggaaaacg aagtgagcca gtatgaaacc cgctatggcc cgctgggcgg cggcaaagtg   240
ggtggatcat taattaacac tgttgaaagt tgtttagcaa aacctcatac agaaaattca   300
t                                                                   301
```

<210> SEQ ID NO 13
<211> LENGTH: 301
<212> TYPE: DNA
<213> ORGANISM: Artificial Sequence
<220> FEATURE:
<223> OTHER INFORMATION: Synthetic Polynucleotide

<400> SEQUENCE: 13

```
cgccggcgtg tagtagtagt ggtagtgccc cggcgtcttg tttttgagta gagtcttctc    60
ctagacttac cccggcgttg atcaccacct ccgccagacc tttaagcgcg ccgcaaagac   120
gcggtcgcgt tgtggcgcga cgcgtggctt caccgccttg accttgtcct tcacgtcgcg   180
gaccttttgc ttcactcggt catactttgg gcgataccgg gcgacccgcc gccgtttcac   240
ccacctagta attaattgtg acaactttca acaaatcgtt ttggagtatg tcttttaagt   300
a                                                                  301
```

<210> SEQ ID NO 14
<211> LENGTH: 99
<212> TYPE: PRT
<213> ORGANISM: Artificial Sequence
<220> FEATURE:
<223> OTHER INFORMATION: Synthetic Polypeptide

<400> SEQUENCE: 14

```
Ala Ala Ala His His His His His Gly Ala Ala Glu Gln Lys Leu
1               5                   10                  15

Ile Ser Glu Glu Asp Leu Asn Gly Ala Ala Thr Ser Gly Gly Gly Gly
            20                  25                  30

Leu Glu Ile Arg Ala Ala Phe Leu Arg Gln Arg Asn Thr Ala Leu Arg
        35                  40                  45

Thr Glu Val Ala Glu Leu Glu Gln Val Gln Arg Leu Glu Asn Glu Val
    50                  55                  60

Ser Gln Tyr Glu Thr Arg Tyr Gly Pro Leu Gly Gly Lys Val Gly
65                  70                  75                  80

Gly Ser Leu Ile Asn Thr Val Glu Ser Cys Leu Ala Lys Pro His Thr
                85                  90                  95

Glu Asn Ser
```

<210> SEQ ID NO 15
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 15

```
ggaattgtga gcggataaca attcccctgt agaaataatt ttgtttaact ttaataagga    60
gatataccat ggcacatcac caccaccatc acgtgggtac cggttcgaat gatgacgacg   120
acaagagtcc ggatcccaat tgggagctcg tgtacacggc gcgcctgcag gtcgacaagc   180
ttgcggccgc actcgagtct ggtaaagaaa ccgctgctgc gaaatttgaa cgccagcaca   240
tggactcgtc tactagcgca gcttaattaa cctaggctgc tgccaccgct gagcaataac   300
tagcataacc ccttggggcc tctaaacggg tcttgagggg tttttg                347
```

<210> SEQ ID NO 16
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 16

```
ccttaacact cgcctattgt taaggggaca tctttattaa acaaattgaa attattcct    60
```

```
ctatatggta ccgtgtagtg gtggtggtag tgcacccatg gccaagctta ctactgctgc    120
tgttctcagg cctagggtta accctcgagc acatgtgccg cgcggacgtc cagctgttcg    180
aacgccggcg tgagctcaga ccatttcttt ggcgacgacg ctttaaactt gcggtcgtgt    240
acctgagcag atgatcgcgt cgaattaatt ggatccgacg acggtggcga ctcgttattg    300
atcgtattgg ggaaccccgg agatttgccc agaactcccc aaaaaac                  347
```

<210> SEQ ID NO 17
<211> LENGTH: 349
<212> TYPE: DNA
<213> ORGANISM: Artificial Sequence
<220> FEATURE:
<223> OTHER INFORMATION: Synthetic Polynucelotide

<400> SEQUENCE: 17

```
gcggccgccc tgcatcatca tcatcatcac ggggccgcag gtaagcctat ccctaaccct     60
ctcctcggtc tcgattctac gaatgggggcc gcaactagtg gtggaggcgg tctggaaatt    120
cgcgcggcgt ttctgcgcca gcgcaacacc gcgctgcgca ccgaagtggc ggaactggaa    180
caggaagtgc agcgcctgga aaacgaagtg agccagtatg aaaccgcta tggcccgctg      240 ggcggcggca aagtgggtgg atcattaatt aacctaggct gctgccaccg ctgagcaata    300
actagcataa ccccttgggg cctctaaacg ggtcttgagg ggttttttg               349
```

<210> SEQ ID NO 18
<211> LENGTH: 349
<212> TYPE: DNA
<213> ORGANISM: Artificial Sequence
<220> FEATURE:
<223> OTHER INFORMATION: Synthetic Polynucleotide

<400> SEQUENCE: 18

```
cgccggcggg acgtagtagt agtagtagtg ccccggcgtc cattcggata gggattggga     60
gaggagccag agctaagatg cttaccccgg cgttgatcac cacctccgcc agacctttaa    120
gcgcgccgca aagacgcggt cgcgttgtgg cgcgacgcgt ggcttcaccg ccttgacctt    180
gtccttcacg tcgcggacct tttgcttcac tcggtcatac tttgggcgat accgggcgac    240
ccgccgccgt ttcacccacc tagtaattaa ttggatccga cgacggtggc gactcgttat    300
tgatcgtatt ggggaacccc ggagatttgc ccagaactcc caaaaaac                 349
```

<210> SEQ ID NO 19
<211> LENGTH: 97
<212> TYPE: PRT
<213> ORGANISM: Artificial Sequence
<220> FEATURE:
<223> OTHER INFORMATION: Synthetic Polypeptide

<400> SEQUENCE: 19

```
Ala Ala Ala Leu His His His His His His Gly Ala Ala Gly Lys Pro
 1               5                  10                  15

Ile Pro Asn Pro Leu Leu Gly Leu Asp Ser Thr Asn Gly Ala Ala Thr
                20                  25                  30

Ser Gly Gly Gly Gly Leu Glu Ile Arg Ala Ala Phe Leu Arg Gln Arg
        35                  40                  45

Asn Thr Ala Leu Arg Thr Glu Val Ala Glu Leu Glu Gln Glu Val Gln
    50                  55                  60

Arg Leu Glu Asn Glu Val Ser Gln Tyr Glu Thr Arg Tyr Gly Pro Leu
65                  70                  75                  80
```

-continued

```
Gly Gly Gly Lys Val Gly Gly Ser Leu Ile Asn Leu Gly Cys Cys His
             85              90                  95
Arg
```